United States Patent [19]

Dextraze et al.

[11] Patent Number: 4,994,460
[45] Date of Patent: Feb. 19, 1991

[54] AGENTS FOR TREATMENT OF BRAIN ISCHEMIA

[75] Inventors: Pierre Dextraze, Quebec, Canada; Joseph P. Yevich, Southington, Conn.

[73] Assignee: Bristol-Myers Squibb Co., New York, N.Y.

[21] Appl. No.: 503,197

[22] Filed: Mar. 30, 1990

Related U.S. Application Data

[63] Continuation-in-part of Ser. No. 360,657, Jun. 1, 1989, abandoned.

[51] Int. Cl.$^5$ .................. A61K 31/495; C07D 403/04
[52] U.S. Cl. .................... 514/252; 514/273; 514/275; 544/295; 544/320; 544/321; 544/330; 544/331; 544/332
[58] Field of Search ............... 544/295, 320, 321, 330, 544/331, 332; 514/252, 273, 275

[56] References Cited

U.S. PATENT DOCUMENTS

| | | | |
|---|---|---|---|
| 2,973,360 | 2/1961 | Janssen et al. | 544/295 |
| 3,299,067 | 1/1967 | Regnier et al. | 544/295 |
| 3,808,210 | 4/1974 | Regnier et al. | 544/295 |
| 4,316,899 | 2/1982 | Markwell | 544/295 |
| 4,605,655 | 8/1986 | Yevich et al. | 514/252 |
| 4,711,899 | 12/1987 | Gaudillier | 546/225 |
| 4,857,644 | 8/1989 | Abou-Gharbia | 544/295 |

OTHER PUBLICATIONS

Regnier et al, "Chemical Abstracts", vol. 70, 1969, col. 11717k.
Yevich, et al., "Chemical Abstracts", vol. 104, 1986, col. 109686v.
Gotti, et al., JPET, 247/3, pp. 1211–1221; (1988) (4/9).
Wauquier, et al., in "Drug Development Research", 8, pp. 373–380; (4/14).

Primary Examiner—Glennon H. Hollrah
Assistant Examiner—James H. Turnipseed
Attorney, Agent, or Firm—Richard P. Ryan

[57] ABSTRACT

A series of 5-halopyrimidin-2-ylpiperazinylalkyl derivatives having useful anti-ischemic properties for treatment and prevention of dirorders resulting from brain and/or spinal cord anoxia.

40 Claims, No Drawings

AGENTS FOR TREATMENT OF BRAIN ISCHEMIA

CROSS REFERENCE

This is a continuation-in-part of U.S. Ser. No. 07/360,657 filed June 1, 1989, now abandoned.

BACKGROUND OF THE INVENTION

This invention pertains to heterocyclic carbon compounds having drug and bio-affecting properties and to their preparation and use. In particular, the invention is concerned with 1,4-disubstituted piperazine derivatives wherein one substituent is a 5-halopyrimidin-2-yl moiety and the other is a carbon chain bearing a carbocycle or heterocycle moiety at its terminus, usually via a linking hetero atom or functional group moiety.

Related art may be viewed in light of the following general structural Formula 1.

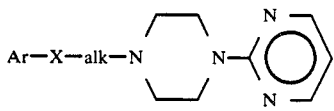
(1)

in which Ar is an aromatic ring, usually phenyl; X is a carbonyl or carbinol group; alk is an alkylene chain.

The most closely related art would appear to be U.S. Pat. No. 4,605,655, issued to Yevich, et al., on Aug. 12, 1986. This patent disclosed and claimed piperazinylbutyrophenone derivatives possessing neuroleptic properties and characterized by structural Formula 2.

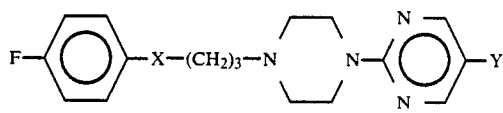
(2)

wherein X is

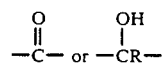

With R being $C_{1-4}$ alkyl, hydrogen or fluorophenyl; and Y is hydrogen or halogen. The instant anti-ischemic compounds are distinguished from these art compounds either by the nature of the terminal carbocyclic ring system, the nature of X, the presence of an alkylene bridge on the piperazine ring and the nature of the $R^3$ substituent.

In U.S. Pat. No. 2,973,360, issued Feb. 28, 1961, a series of CNS depressant compounds is disclosed with Ar being 2-thienyl; X being carbonyl or carbinol; and alk being $C_2$ and $C_3$ alkylene. The most pertinent compound specifically exemplified and claimed in this patent is shown below as structure (3).

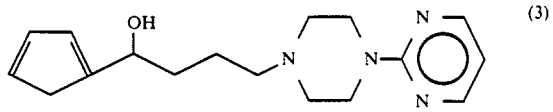
(3)

The following references, while related, are felt to be less relevant to the new compounds disclosed in this application.

Reginer, et al., U.S. Pat. No. 3,299,067, issued Jan. 17, 1967 discloses compounds comprising a benzyl-type moiety attached to the 2-pyrimidinylpiperazine. A specific example of this series which is said to be useful as peripheral vasodilators, analgesics and antiinflammatory agents, is shown below as structure (4).

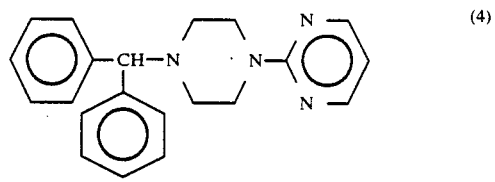
(4)

U.S. Pat. No. 3,802,210 issued to Regnier, et al., in April 1974 relates to a series of aryloxypropanolamine antihypertensive compounds having a pyrimidinylpiperazine moiety as in (5). However, these compounds are not butyrophenones or close analogs.

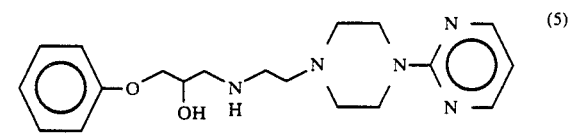
(5)

U.S. Pat. No. 4,316,899 issued to Markwell on Feb. 23, 1982 relates to another series of aryloxypropanolamine antihypertensive compounds containing a pyrimidinylpiperazine moiety as exemplified by structure (6)

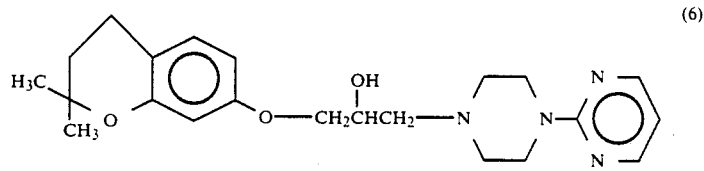
(6)

Gotti, et al., JPET, 247/3, pages 1211–1221 (1988); have disclosed that ifenprodil and a derivative are effective in tissue sparing in animal models of stroke and brain infarction.

IFENPRODIL

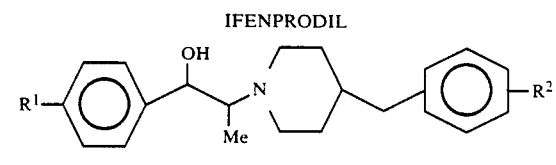

$R^1$ = OH, $R^2$ = H

Wauquier, et al., in "Drug Development Research", 8/373–380 (1986) disclosed that Sabeluzole (R 58,735) is a potent antihypoxic agent with anticonvulsant properties.

SABELUZOLE

A series of anti-anoxic 2-[4-benzoyl-1-piperidinyl)-1-phenylalkanol derivatives, having some structural resemblance to ifenprodil type compounds, is disclosed in U.S. Pat. No. 4,711,899 issued in December, 1987 to Gaudilliere, et al.

There is nothing in these references, or in the general prior art, to suggest the anti-ischemic compounds of the present invention.

SUMMARY AND DETAILED DESCRIPTION OF THE INVENTION

In its broadest aspect, the present invention is concerned with 5-halopyrimidin-2-yl piperazine derivatives having anti-ischemic properties characterized by a compound of Formula I

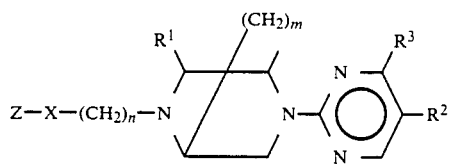

wherein Z is a member selected from the group consisting of

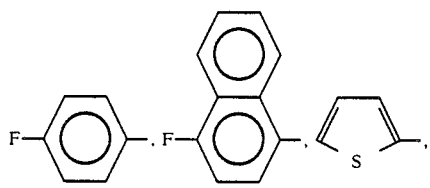

naphthalenyl, anthracenyl, fluorenyl, phenanthrenyl, and $C_{5-6}$ cycloalkyl. X is a member selected from the group consisting of —O—, —S—, —SO$_2$—, —CO—,

wherein $R^4$ is hydrogen, $C_{1-4}$ alkyl, and —CHR$^5$— wherein $R^5$ is hydrogen, CN, or NHR$^6$ with $R^6$ being acetyl,

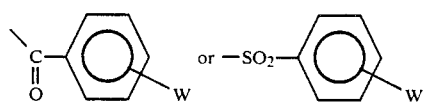

wherein W is hydrogen, halogen or alkoxy; or Z and X taken together can be

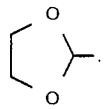

$R^1$ is hydrogen or $C_{1-4}$ alkyl; $R^2$ is halogen; and $R^3$ is hydrogen, $C_{1-4}$ alkoxy or $C_{1-4}$ alkylthio. The symbol n is the integer 1-3 and the symbol m is the integer 0 or 1. There is a proviso for the compounds of Formula I which is that Z cannot be when X is

or —CO— while $R^3$ is either hydrogen or $C_{1-4}$ alkoxy, or while m is 0.

It is to be understood that pharmaceutically acceptable salts and/or solvates of the Formula I compounds also comprise the present invention. Further, as used herein, halogen denotes chlorine, bromine, iodine and preferably fluorine. Preferred compounds are those wherein Z is p-fluorophenyl and wherein X is —CH-R$^5$—.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series. Separation of the individual isomers is accomplished by application of various methods which are well known to practitioners in the art.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of structure I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, pamoic acid, cyclamic acid, pivalic acid and the like; useful inorganic acids are hydrohalide acids such as HCl, HBr, HI; sulfuric acid; phosphoric acid and the like. The preferred solvate forms of Formula I compounds are hydrates.

The compounds of the present invention are useful pharmacologic agents with anti-ischemic properties. Brain cells are particularly vulnerable to damage caused by ischemic conditions. Brain ischemia, or insufficient oxygen, may result from injury or disease and may last from only transient periods of time to periods of lengthy duration, as in stroke. In this regard, the compounds of Formula I are useful for treatment and prevention of injury to the brain and spinal cord and of edema due to head trauma, stroke, arrested breathing, cardiac arrest, Reye's syndrome, cerebral thrombosis, embolism, hemorrhage or tumors, encephalomyelitis, spinal cord injury, hydroencephalis, and post-operative brain injury.

The anti-ischemic activity of the compounds of Formula I have been demonstrated in certain pharmacologic tests and model systems that are used to determine drug effects on brain ischemia and its aftermath. Most specifically, administration of the compounds of Formula I results in protecting against hypoxia-induced death in an anoxic nitrogen test in rats. This particular test identifies the neuro-protective effects of substances against lethal brain damages produced by a lack of oxygen consumption (anoxia). In this test procedure, control animals exposed for one minute to a pure nitrogen atmosphere will expire because of respiratory failure caused by irreversible damage to the brain respiratory center. The animals exhibit strong heartbeat following anoxia exposure. To demonstrate effectiveness, experimental compounds must antagonize the anoxic insult resulting in survivability of the test animals.

One aspect then of the present invention involves administration of a compound of Formula I or a pharmaceutically acceptable acid and/or solvate thereof, to a mammal suffering from ischemia or being susceptible to ischemia. In general the compound would be given in a dose range of from about 0.1 mg/kg to about 10 mg/kg body weight.

Although the dosage and dosage regimen of a Formula I compound must in each case be carefully adjusted, utilizing sound professional judgment and considering the age, weight and condition of the recipient, the route of administration and the nature and extent of the ischemia, generally, the daily dose for human use will be from about 0.1 g to about 10 g, preferably 0.5 g to 5 g, when given orally. In some instances, a sufficient therapeutic effect can be obtained at lower doses while in others, larger doses will be required. As is apparent to one skilled in clinical pharmacology, the amount of a Formula I compound comprising the daily dose may be given in a single or divided dose, taking into account those principles understood by the skilled practitioner and necessary for his practice of the art.

The term "systemic administration" as used herein refers to oral, sublingual, buccal, transnasal, transdermal, rectal, intramuscular, intravenous, intraventricular, intrathecal, and subcutaneous routes. Generally, it will be found that when a compound of the present invention is administered orally a slightly larger quantity of the active drug may be required to produce the same effect as a somewhat smaller quantity when given parenterally. In accordance with good clinical practice, it is preferred to administer the instant compounds at a concentration level which will produce effective beneficial effects without causing any harmful or untoward side effects.

Therapeutically, the instant compounds are generally given as pharmaceutical compositions comprised of an effective ischemia-protective amount of a Formula I compound or a pharmaceutically acceptable acid addition salt and/or hydrate thereof and a pharmaceutically acceptable carrier. Pharmaceutical compositions for effecting such treatment will contain a major or minor amount (e.g. from 95% to 0.5%) of at least one compound of the present invention in combination With a pharmaceutical carrier, the carrier comprising one or more solid, semi-solid, or liquid diluent, filler and formulation adjuvant which is non-toxic, inert and pharmaceutically acceptable. Such pharmaceutical compositions are preferably in dosage unit forms; i.e., physically discrete units having a pre-determined amount of the drug corresponding to a fraction or multiple of the dose which is calculated to produce the desired therapeutic response. In usual practice, the dosage units contain 1, ½, ⅓, or less of a single dose. A single dose preferably contains an amount sufficient to produce the desired therapeutic effect upon administration at one application of one or more dosage units according to the pre-determined dosage regimen, usually a whole, half, third, or less of the daily dosage administered once, twice, three, or more times a day. It is envisioned that other therapeutic agents can also be present in such a composition. Pharmaceutical compositions which provide from 0.1 to 1 g of the active ingredient per unit dose are preferred and are conventionally prepared as tablets, lozenges, capsules, powders, aqueous or oily suspensions, syrups, elixirs, and aqueous solutions. Preferred oral compositions are in the form of tablets, capsules, and may contain conventional excipients such as binding agents. (e.g., syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from about 0.1% to 10% by weight of a Formula I compound or one of its salt forms in water or a vehicle consisting of a polyhydric aliphatic alcohol such as glycerine, propylene glycol, and the polyethylene glycols or mixtures thereof. The polyethylene glycols consist of a mixture of non-volatile, usually liquid, polyethylene glycols which are soluble in both water and organic liquids and which have molecular weights from about 200 to 1500.

When transnasal application is intended, the Formula I compound pharmaceutical composition is formulated in a pharmaceutical composition which enhances penetration of the nasal mucosa. Such formulations normally employ fatty acid salts of the Formula I base compound and their preparation and use would be known to one skilled in the pharmaceutical arts.

The general procedures for preparation of Formula I compounds are outlined in Schemes 1 and 2. In these schemes the symbols A and B refer to subclasses of the moieties denoted by X supra.

Scheme 1

General Leading to Formula I Compounds

Z—A—(CH$_2$)$_n$—W +

III

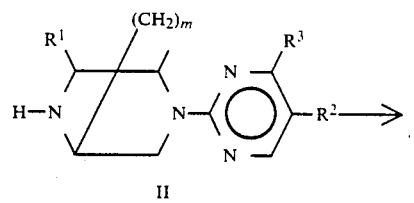

II

-continued

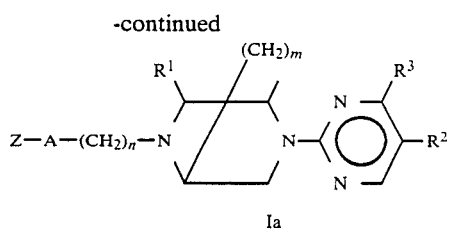

Ia

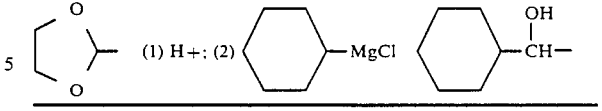

In scheme 1: Z, $R^1$-$R^3$, m and n are as previously defined. The symbol A represents O, S, CO and $CH_2$ and symbol W represents a leaving group, as well understood in organic synthesis, such a leaving group being preferably chloride or bromide. In addition Z and A can be taken together as a ketal such as dioxolans. The intermediate compounds II and III are known in the literature but some synthetic examples will also be given hereinbelow for convenience in preparing the product compounds of the present invention.

In particular, synthesis of Formula II intermediates as well as some IA analogs are disclosed in U.S. Pat. No. 4,605,655 which is incorporated herein in its entirety. As covered in U.S. Pat. No. 4,605,655, when preparing IA wherein A is CO, the carbonyl group is generally protected as the ketal derivative.

Scheme 2 outlines chemical conversions of IA product compounds to IB product compounds by transformation of certain X moieties (IA→IB).

Scheme 2

Variation of X in Formula I Compounds

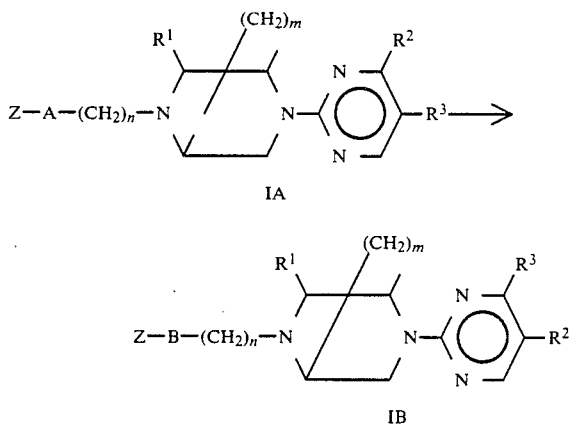

| | Transformations | |
|---|---|---|
| A | Reaction | B |
| S | oxidation, e.g. $H_2O_2$ | $SO_2$ |
| CO | reduction, e.g. $NaBH_4/EtOH$ | CHOH |
| CO | reductive alkylation e.g. $R^4MgCl$ | $CR^4OH$ |
| CO | Tosylmethylisocyanide | CHCN |
| CHOH | $Ph_3P/(i-PrO_2C-N)_2/$ $(PhO)_2PON_3$ | $N_3$ |
| $N_3$ | cat. $H_2$ | $NH_2$ |
| $NH_2$ | acylation or sulfonylation | $NHR^6$ |
| Z-A | | Z-B |

In scheme 2, Z, $R^1$-$R^3$, A, n and m are as previously defined and symbol B represents other values of X such as $SO_2$, $CR^4OH$ and $NHR^6$. Additionally B can be $N_3$ and $NH_2$, thereby giving 2 synthetic intermediates in the process of converting X=CHOH to X=CHNHR$^6$ in Formula I compounds.

DESCRIPTION OF SPECIFIC EMBODIMENTS

The compounds which constitute this invention and their methods of preparation will appear more full from a consideration of the following examples which are given for the purpose of illustration only and are not to be construed as limiting the invention in sphere or scope. All temperatures are understood to be in degrees C. when not specified.

The nuclear magnetic resonance (NMR) spectral characteristics refer to chemical shifts (δ) expressed as parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs), singlet (s), multiplet (m), doublet (d), doublet of doublets (dd), or quartet (q). Abbreviations employed are DMSO-$d_6$ (deuterodimethylsulfoxide), $CDCl_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

SYNTHESIS OF INTERMEDIATES

Example 1

γ-Chloro-p-fluorobutyrophenone ethylene ketal

A solution of γ-chloro-p-fluorobutyrophenone (50 g. 025 mole, commercially available); ethylene glycol (50 mL); p-toluene sulfonic acid (0.1 g) in 300 mL benzene is refluxed for 18 h with water of reaction being removed by means of a Dean Stark water trap. Upon cooling to room temperature, the reaction mixture is washed with dilute sodium bicarbonate, dried ($MgSO_4$), filtered and the benzene removed by concentration in vacuo. The residual oil was distilled to give 57.7 g (93%) of product, b.p. 106-112/0.01 Torr.

Example 2

1-(5-Fluoro-2-pyrimidinyl)piperazine (1) Ethyl 4-(5-fluoro-4-methylthio-2-pyrimidinyl)-1-piperazine carboxylate: A mixture of 2-chloro 5-fluoro-4-methylthiopyrimidine (28.3 g, 0.16 mole), N-carbethoxypiperazine (25.26 g, 0.16 mole), anhydrous $K_2CO_3$ (66.0 g) and a catalytic amount of KI in MeCN (400 mL) was stirred and heated under reflux for 18 h. The hot reaction mixture was filtered, concentrated in vacuo and the residue crystallized from EtOH to give 29.8 g (62%) of intermediate product.

(2) Ethyl 4-(5-fluoro-2-pyrimidinyl)-1-piperazine carboxylate: A mixture of ethyl-4-(5-fluoro-4-methylthio-2-pyrimidinyl)-1-piperazine carboxylate (29.8 g 0.1 mole) and Raney Nickel catalyst (15 tsp) in EtOH (550 mL) was stirred and heated under reflux for 48 h. The reaction mixture was filtered, concentrated in vacuo and the residue recrystallized twice from EtOH to provide 11.2 g (45%) of product, m.p. 104°–107° C.

A solution of this ester intermediate (11.2 g, 0.04 mole) in 6N HCl (100 ml) was stirred and heated under reflux overnight. The cooled reaction mixture was made alkaline by addition of 50% NaOH, extracted with $Et_2O$ and the extract dried ($MgSO_4$) and concentrated in vacuo to provide 7.23 g (100%) of product as a viscous oil which was treated with ethanolic HCl in EtOH to yield the hydrochloride salt, m.p. 250°–252° C.

Anal. Calcd. for $C_8H_{11}FN_4$·HCl: C, 43.95; H, 5.54; N, 25.63. Found: C, 44.23; H, 5.57; N, 25.38.

Example 3

5-Bromo-2-(1-piperazinyl)pyrimidine

To an ice-cooled solution of 1-(2-pyrimidinyl) piperazine (16.4 g, 0.1 mole) in 1N HCl (100 mL) was added dropwise bromine (15.98 g, 0.1 mole). After stirring at 0° for 0.5 h. the mixture was heated to 100° C. until dissipation of the red color had occurred. The mixture was filtered, cooled, made alkaline with 50% NaOH and extracted with $Et_2O$. The dried extract ($MgSO_4$) was concentrated in vacuo to provide 14.5 g (62%) of product, m.p. 73°–75° C.

By appropriate modification of this procedure the 5-chloro intermediate and the 5-iodo intermediate may be prepared.

Example 4

1-(4-Fluorophenyl)-4-[4-(5-fluoro-2-pyrimidinyl)-1-piperazinyl]butanone hydrochloride (IA)

A mixture of 1-(5-fluoro-2-pyrimidinyl)piperazine (7.3 g, 0.04 mole), γ-chloro-p-fluorobutyrophenone ethylene ketal (14.5 g, 0.06 mole), anhydrous $K_2CO_3$ ( 24.8 g) and a catalytic amount of KI in MeCN (100 mL) was stirred and heated under reflux for 36 h. The hot mixture was filtered, concentrated in vacuo and the residue treated with 20 mL of 3N HCl and 100 mL EtOH. After cooling in ice, the product was collected by filtration and dried to give 7.6 g (50%) of product as a white solid, m.p. 234°–236° C.

Anal. Calcd. for $C_{18}H_{20}F_2N_4O$·HCl: C, 56.48; H, 5.53; N, 14.64. Found: C, 56.27; H, 5.52; N, 14.27.

$^1$H NMR (DMSO-$d_6$): 2.10 (2,m); 3.20 (6,m); 3.54 (4,m); 4.58 (2,m); 7.34 (2,m); 8.08 (2,m); 8.55 (2,s); 11.60 (1. bs).

IR (KBr): 960, 1235, 1245, 1365, 1510, 1560, 1600, 1680, 2550, and 2920 cm$^{-1}$.

Example 5

1-(4-Fluorophenyl)-4-[4-(5-fluoro-2-pyrimidinyl)-1-piperazinyl]-butanol hydrochloride (IB)

A mixture of the Ia compound prepared above in Example 4 (7.6 g 0.02 mole) and $NaBH_4$ (2.3 g, 0.06 mole) in EtOH (650 mL) was stirred overnight. The mixture was treated with ethanolic HCl, stirred at room temperature for 1.5 h. then heated to reflux. Solvent was removed in vacuo and to the residue was added 1N NaOH and $CH_2Cl_2$. The organic layer was separated, dried ($MgSO_4$) and concentrated in vacuo. This residue was dissolved in EtOH (treated with ethanolic HCl and cooled). The hydrochloride salt was collected by filtration and dried to afford 6.2 g (81%) of product, m.p. 236°–238° C.

Anal. Calcd. for $C_{18}H_{22}F_2N_4O$·HCl: C, 56.18; H, 6.03; N, 14.56 Found: C, 55.98; H, 6.06; N, 14.23

$^1$H NMR (DMSO-$d_6$): 1.71 (2,m); 3.10 (4,m); 3.47 (4,m); 4.59 (3,m); 5.30 (1.bs); 7.11 (2,m); 7.40 (2,m); 8.53 (2,s); 11.50 (1.bs).

IR (KBr), 955, 1220, 1235, 1370, 1440, 1455, 1480, 1510, 1560, 1605, 2600 and 2920 cm$^{-1}$.

Example 6

1-[3-[2-(4-fluorophenyl)-1,3-dioxolan-2-yl]propyl]-4-(5-fluoro-2-pyrimidinyl)piperazine hydrochloride (IA)

(1) A mixture of the γ-chloro ketal (Ex. 1: 27.49 g, 0.112 mole), piperazine (48.24 g, 0.56 mole), $K_2CO_3$ (46.43 g, 0.33 mole), and a catalytic amount of KI in 358 mL of MeCN was refluxed for 18 h. The hot reaction mixture was filtered and the filtrate concentrated in vacuo to a residue which was partitioned between water (250 mL) and $Et_2O$. The water layer was extracted further with $Et_2O$, the extracts combined and dried ($MgSO_4$) and concentrated in vacuo to give 28.5 g of 1-[3-[2-(4-fluorophenyl)-1.3-dioxolan-2-yl]propyl]-piperazine.

(2) This piperazine intermediate (7.8 g, 0.026 mole), 2-chloro-5-fluoro-4-methylthiopyrimidine (4.73 g, 0.026 mole), pulverized $K_2CO_3$ (11.05 g) and a catalytic amount of KI in 80 mL MeCN was refluxed 18 h. The hot reaction mixture was filtered and the filtrate was concentrated in vacuo to give 11.1 g of residue which was flash-chromatographed on silica gel (3% MeOH/$CH_2Cl_2$). Appropriate fractions were combined, dissolved in 10 mL EtOH, chilled and treated with ethanolic HCl from which 1.5 g of 1-[3-[2-(4-fluorophenyl)-1,3-dioxolan-2-yl]propyl]-4-(5-fluoro-2-methylthio-2-pyrimidinyl)piperazine hydrochloride, m.p. 233°–235° C. was obtained.

Anal. Calcd. for $C_{21}H_{26}F_2N_4O_2S$·HCl: C, 53.33; H, 5.75; N, 11.85. Found: C, 53.53; H, 5.81; N, 12.03.

(3) 1-[3-[2-(4-fluorophenyl)-1,3-dioxolan-2-yl]propyl]-4-(5-fluoro-2-methylthio-2-pyrimidinyl)piperazine hydrochloride (7.45 g, 0.0.17 mole), triethylamine (3.05 g, 0.034 mole) and 2 teaspoons of Raney Nickel in water were mixed in EtOH (125 mL) and refluxed 18 h. The hot reaction mixture was filtered and the filtrate was concentrated in vacuo to about 1/5 volume. A crude crystalline product was obtained by filtration and its recrystallization from 20–25 mL EtOH gave 1.6 g of solid, m.p. 220°–222° C. This solid was converted to the hydrochloride salt in EtOH using ethanolic HCl. Filtration and drying gave 1.6 g of product, m.p. 242°–244° C.

Anal. Calcd. for $C_{20}H_{24}F_2N_4O_2$·HCl: C, 56.27; H, 5.90; N, 13.12. Found: C. 56.12; H, 6.06; N, 12.90.

Example 7

Preparation of 2-(5-fluoro-2-pyrimidinyl)-(1S,4S)-2,5-diazabicyclo[2.2.1]heptane (1) Trans-4-hydroxy-1-(4-toluenesulfonyl)-L-proline. To a solution of hydroxy-L-proline (80 g, 0.61 mole) in 2N NaOH (800 mL) was added tosylchloride (136.1 g, 0.71 mole) in $Et_2O$ (700 mL). The reaction mixture was stirred at 0° C. for 1.5 h and continued for an additional 3.5 h at 23° C. The aqueous layer was separated, acidified with concentrated HCl to pH 1 and allowed to stand at −10° C. for 12 h. The precipitate was filtered, washed with cold water, and concentrated in vacuo to a volume of 300 mL. The precipitate obtained was combined with the previous precipitate, and the combined solids were recrystallized from ethylacetate. Drying in vacuo at 50° C. for 24 h afforded trans-4-hydroxy-1-(4-toluenesulfonyl)-L-proline (107.38 g, 62%).

(2) Potassium salt of trans-4-hydroxy-1-(4-toluenesulfonyl)-L-proline. To a solution of trans-4-hydroxy-1-(4-toluenesulfonyl)-L-proline (107.38 g, 0.376 mole) in acetone (450 mL) was added potassium 2-ethylhexanoate in BuOH (1.91N; 189.5 mL). After standing at 23° C. for 20 min, the insoluble material was filtered and the resulting solution was concentrated to 320 mL. $Et_2O$ (1000 mL) was added to the concentrate and the solvents removed under reduced pressure yielding a solid (122.90 g). The hygroscopic product was used in the next step without further purification.

(3) 1N-Tosylhydroxy-L-proline methyl ester. To a solution of potassium trans-4-hydroxy-1-(4-toluenesulfonyl)-L-proline (122.90 g, 0.376 mole) in 250 mL of N,N-dimethylacetamide was added $CH_3I$ (24.5 mL, 0.39 mole) while under $N_2$ atmosphere. The light protected mixture was stirred 16 h. The mixture was poured onto ice water and extracted with $CH_2Cl_2$ (3×400 mL). The combined organic extracts were washed with 2% $NaHCO_3$ (400 mL), $H_2O$ (4×1.5 L), dried over $MgSO_4$, filtered, and concentrated under reduced pressure to leave a viscous oil. The crude oil was triturated with petroleum ether to give N-tosylhydroxy-L-proline methyl ester as a pale yellow solid (63.20 g, 56.2%) which was used in the next step without further purification.

(4) (2S,4R)-1-(4-toluenesulfonyl)-2-hydroxymethyl-4-hydroxy pyrrolidine. To a solution of N-tosylhydroxy-L-proline methyl ester (62.20 g, 0.21 mole) in THF (600 mL) at 0° C. was added $LiBH_4$ (15.8 g, 0.73 mole) in small portions. The reaction mixture was stirred at 0° C. for 1 h and allowed to stand ... ° C. for 18 h. The reaction mixture was cooled to -20° C., made neutral with 6N HCl and concentrated under reduced pressure. The residue was treated with water (550 ml) and extracted with EtOAc (4×300 mL). The combined organic extracts were washed with $H_2O$, dried over $MgSO_4$, filtered and concentrated under reduced pressure to give N-tosylhydroxy-L-prolinol as a white solid (50.56 g, 88.8%) which was used in the next step without further purification.

(5) (2S,4R)-1-(4-toluenesulfonyl)-2-4-toluenesulfonyloxymethyl)-4-(4-toluenesulfonyloxy)-pyrrolidine. To a solution of p-toluenesulfonyl chloride (155 g, 0.81 mole) in pyridine (330 mL) at 0° C. was added N-tosylhydroxy-L-prolinol (104.40 g, 0.39 mole). The reaction mixture kept at 6° C. for 72 h and then poured into cold 2N HCl (2.5L). The aqueous layer was extracted with $CH_2Cl_2$ (3×1000 mL). The combined organic extracts were dried over $MgSO_4$, filtered, and concentrated under reduced pressure to give an oil. The oil was triturated with EtOH and the solid that formed was collected by filtration. The crude product was recrystallized from EtOH (3.5 L) to give tritosylhydroxy-L-prolinol (99.87 g, 44.2%, m.p. 130°-132° C., $[\alpha]_D^{24} = 57.1$, c = 1.2, acetone).

(6) (1S,4S)-2-(4-toluenesulfonyl)-5-phenylmethyl-2,5-diazabicyclo[2.2.1]heptane. To a suspension of tritosylhydroxy-L-prolinol (98.87 g, 0.17 mole) in toluene (350 mL) was added benzylamine (54.83 g, 0.51 mole). The resulting mixture was heated at reflux for 18 h and allowed to cool to 23° C. The reaction mixture was filtered and the solvent removed under reduced pressure. The residue was triturated with EtOH and the solid that formed was collected by filtration to give (1S,4S)-2-(4-toluenesulfonyl)-5-phenylmethyl-2,5-diazabicyclo[2.2.1]heptane (54.18 g, 93.2%) which was used in the next step without further purification.

(7) (1S,4S)-N-benzyl-2,5-diazabicyclo[2.2.1]heptane dihydrobromide. A mixture of (1S,4S)-2-(4-toluenesulfonyl)-5-phenylmethyl-2,5-diazabicyclo[2.2.1]heptane (54.0 g, 0.16 mole) in AcOH (830 mL) containing HBr (30% wt.) was heated at 70° C. for 1% h. The reaction mixture was allowed to cool and concentrated under reduced pressure to a final volume of ca. 300 mL. The precipitate that formed was filtered and washed with acetone to give (1S,4S)-N-benzyl-2,5-diazabicyclo[2.2.1]heptane (50.30 g, 91.3%, m.p. 272°-275° C.).

Anal. Calcd. for $C_{12}H_{16}N_2 \cdot 2HBr$: C, 41.17; H, 5.19; N, 8.01. Found: C, 40.83; H, 5.16; N, 8.06.

(8) 2-(tert-butyloxycarbonyl)-5-phenylmethyl-(1S,4S)-2,5-diazabicyclo[2.2.1]heptane. The title compound was prepared as described for the 1R,4R isomer Ex. 8 (10) yield: 8.30 g.

(9) 2-(t-butyloxycarbonyl)-(1S,4S)-2,5-diazabicyclo 2.2.1]heptane. Into a solution of the (8) intermediate (8.30 g, 28.82 mmol) in 250 mL of EtOH was added AcOH (3.2 mL). The reaction mixture was treated with 10% palladium-on-carbon (2.40 g) and hydrogenated at 50 psi for 6 h at 23° C. The same workup procedure as described for the 1R,4R isomer was followed. Yield 5.60 g, 98.1%. The product was used in the next step without purification.

(10) 2-(t-butyloxycarbonyl)-5-(5-fluoro-4-methylthio-2-pyrimidinyl)-(1S,4S)-2,5-diazabicyclo[2.2.1]heptane (4.50 g, 22.73 mmol), 2-chloro-5-fluoro-4-methylthiopyrimidine [4.64 g (87.5% pure), 22.73 mmol], micropulverized $K_2CO_3$ (9.40 g, 68.19 mmol), and KI (0.57 g, 3.41 mmol) in 65 mL of MeCN was refluxed for 44 h. The reaction mixture was concentrated under reduced pressure and the residue was dissolved in a minimum amount of $H_2O$. The solution was extracted with $CH_2Cl_2$, washed with saturated NaCl solution, dried over $K_2CO_3$, filtered and concentrated under reduced pressured. Flash chromatography (Hexane:EtOAc; 4:1) gave the title compound (6.60 g, 85.4%).

(11) 2-(5-fluoro-2-pyrimidinyl)-(1S,4S)-2,5-diazabicyclo[2.2.1]heptane. A mixture of intermediate (10) compound (6.50 g, 19.12 mmol) and Raney Ni (5 scoops) in 100 mL EtOH was refluxed for 48 h. Raney Ni was filtered through a celite pad and the filtrate was concentrated to give 2-(t-butyloxycarbonyl)-5-(5-fluoro-2-pyrimidinyl)-(1S,4S)-2,5-diazabicyclo[2.2.1]heptane (5.31 g, 94.5%). The product (4.94 g, 16.80 mmol) was dissolved in 3N HCl (100 mL) and refluxed for 3h. The reaction mixture was concentrated under reduced pressure. The residue was made basic with 5N NaOH solution and extracted with $CH_2Cl_2$ (4×100 mL). The combined CH extracts were dried over $K_2CO_3$, and concentrated under reduced pressure to give the title compound (2.85 g, 87.4%).

Example 8

Preparation of (1R,4R)-2,5-diazabicyclo[2.2.1]heptane dihydrobromide (1) Allo-4-hydroxy-D-proline Hydrochloride. A solution of acetic anhydride (380 mL) in glacial AcOH (1.2 L) was heated to 50° C. and 4-hydroxy-L-proline

United States Patent Office

PTO - BOYERS, PA Duty Station

MISSING PAGE TEMPORARY NOTICE

PATENT # 4994460   FOR ISSUE DATE 2-19-91

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

COLUMN # 13-14

Data Conversion Operation
Boyers, Pa drogenation was continued for 2 h. After this time, heating was discontinued; the reaction mixture was allowed to cool to room temperature and hydrogenation was continued for 3 h. The reaction mixture was filtered through celite and the filtrate was concentrated under reduced pressure. The residue was made alkaline by the addition of 5N NaOH and extracted with $CH_2Cl_2$ (5×100 mL). Combined $CH_2Cl_2$ extracts were dried over $K_2CO_3$, filtered and concentrated under reduced pressure to give the title compound (2.34 g, 93.2%). The product was used in the next step without further purification.

(12) 2-(t-butyloxycarbonyl)-5-(5-fluoro-4-methylthio-2-pyrimidinyl)-(1R,4R)-2,5-diazabicyclo[2.2.1]heptane. The title compound was prepared as described for the 1S,4S isomer Example 7 (10). Yield: 6.80 g, 88.2%.

(13) 2-(5-fluoro-2-pyrimidinyl)-(1R,4R)-2,5-diazabicyclo[2.2.1]heptane. The title compound was prepared as described for the 1S,4S isomer Example 7 (11). Yield: 2.74 g, 88.4%.

Other intermediates and starting materials used for preparation of Formula I compounds are either available commercially or are readily available to one skilled in the art via the chemical literature or by appropriate modification of the foregoing examples.

SYNTHESIS OF PRODUCTS

Formula IA Compounds

Example 9

1-(4-(4-Fluorophenyl)butyl)-4-(5-fluoro-2-pyrimidinyl) piperazine

A mixture of 4-(5-fluoro-2-pyrimidinyl)piperazine (1.66 g, 9.1 mmol), 1-chloro-4-(4-fluorophenyl)butane[1] (1.68 g, 9.0 mmol), $K_2CO_3$ (2.48 g, 17.9 mmol), KI (0.15 g, 0.9 mmol) and MeCN (90 mL) was refluxed under $N_2$ atm. for 40 h and then allowed to cool at 23° C. and filtered; the solids were washed with MeCN (2×20 mL). The filtrates were combined and concentrated under reduced pressure to a gum which was dissolved in EtOAc (200 mL). The organic solution was washed with water (20 mL), dried ($MgSO_4$) and concentrated under reduced pressure. The residue was passed through a silica gel pad using EtOAc acetate as eluting solvent. The appropriate fractions were combined and concentrated; the resulting solid was recrystallized from ethanol to afford analytical sample; mp 59°–61° C.; $^1H$ NMR ($CDCl_3$, 200 MHz) δ: 1.4–1.8 (m, 4H), 2.2–2.5 (m, 6H), 2.45 (t, J=5.1 Hz), 2.5–2.7 (m, 2H), 3.74 (t, J=5.1 Hz, 4H), 6.9–7.0 (m, 2H), 7.0–7.2 (m, 2H), 8.17 (s, 2H); IR (KBr) ν: 610, 1555, 1511, 1485, 1455, 1445, 1360 cm$^{-1}$;

(1) M. Winn, D. Arendsen, P. Dodge, A. Drew, D. Dunnigan, R. Hallas, K. Hwang, J. Kynel, Yien-Hwei Lee, N. Plotnikoff, P. Young and H. Zaugg. J. Med. Chem., 19(4), 461 (1976).

Anal. Calcd. for $C_{18}H_{22}N_4F_2$: C, 65.04; H, 6.67; N, 16.86. Found: C, 64.95; H, 6.77; N, 16.85.

Example 10

1-[3-(4-Fluorophenylthio)propyl]-4-(5-fluoro-2-pyrimidinyl) piperazine (1) 3-(4-fluorophenylthio)-1-propanol. A mixture of 4-fluorophenylthiol (15 g, 0.117 mole), 3-chloro-1-propanol (10.8 mL, 0.128 mole) and $N^2OH$ (4.96 g, 0.124 mole) in EtOH (120 mL) was refluxed under $N_2$ atm for 20 h, cooled to 23° C. and filtered. The insoluble material was washed with EtOH (10 mL). The filtrate and washings were concentrated under reduced pressure to a crude material (23.3 g) which was distilled under high vacuum, 17.0 g (78%), bp 120°–2° C./0.75 mmHg; $^1H$ NMR ($CDCl_3$, 200 MHz) δ: 1.44 (t, J=5.3 Hz, 1H), 1.75–1.0 (m, 2H), 2.97 (t, J=7.1 Hz, 2H), 3.72 (m, 2H), 6.9–7.1 (m, 2H), 7.3–7.5 (m, 2H); IR (film) ν: 3600–3000, 1590, 1490, 1225 cm$^{-1}$;

Anal. Calcd. for $C_9H_{11}OFS\cdot0.1H_2O$; C, 57.48; H, 6.00; S, 17.05. Found: C, 57.47; H, 5.89; S, 16.73.

(2) 1-bromo-3-(4-fluorophenylthio)propane. A mixture of 3-(4-fluorophenylthio)-1-propanol (9.1 g, 48.9 mmol), aqueous HBr (48%, 14 mL) and conc. aqueous $H_2SO_4$ (2.4 mL) was refluxed for 24 h, cooled and carefully poured onto ice-water mixture (120 mL). The aqueous phase was extracted with $Et_2O$ (3×25 mL). The $Et_2O$ layer was dried ($MgSO_4$) and concentrated to a crude oil which was distilled under high vacuum, 6.9 g, (57%), bp 108°–114° C./0.6 mmHg; $^1H$ NMR ($CDCl_3$, 200 MHz) δ: 2.0–2.2 (m, 2H), 3.00 (t, J=6.9 Hz, 2H), 3.50 (t, J=6.3 Hz, 2H), 6.9–7.1 (m, 2H), 7.3–7.5 (m, 2H); IR (film) ν: 1590, 1490, 1225 cm$^{-1}$;

Anal. Calcd. for $C_9H_{10}BrFS$: C, 43.39; H, 4.05. Found: C, 41.31; H, 3.88.

(3) A mixture of 4-(5-fluoro-2-pyrimidinyl)piperazine (1.58 g, 8.67 mmol), 1-bromo-3-(4-fluorophenylthio)-propane (2.16 g, 8.67 mmol), triethylamine (1.33 mL, 9.53 mmol) and KI (1.58 g, 9.52 mmol) in MeCN (45 mL) was refluxed under $N_2$ atm. for 18 h, then cooled at 23° C. and concentrated under reduced pressure. The residue was solubilized in EtOAc (400 mL) and the resulting organic solution was washed with water (2×40 mL), dried ($MgSO_4$) and concentrated to dryness. The crude material (3.0 g) was purified on a silica gel pad (3.4×8.5 cm) using a mixture of 50%–100% EtOAc in hexane. Appropriate fractions were combined and concentrated leaving 2.64 g (87%) mp 68°–70° C. Recrystallization from EtOH afforded an analytical sample, mp 70°–1° C.; $^1H$ NMR ($CDCl_3$, 200 MHz) δ: 1.6–1.9 (m, 2H), 2.2–2.7 (m, 6H), 2.92 (t, J=7 Hz, 2H), 3.6–3.9 (m, 4H), 6.9–7.1 (m, 2H), 7.3–7.5 (m, 2H), 8.17 (s, 2H); IR (KBr) ν: 1609, 1552, 1500, 1490 cm$^{-1}$;

Anal. Calcd. for $C_{17}H_{20}N_4SF_2$: C, 58.27; H, 5.75; N, 15.99; S, 9.15. Found: C, 58.21; H, 5.73; N, 15.87; S, 9.43.

Example 11

1-[3-(1,3-dioxolan-2-yl)propyl]-4-(5-Fluoro-2-pyrimidinyl) piperazine

A mixture of 4-(5-fluoro-2-pyrimidinyl)piperazine (7.29 g, 40.0 mmol), 2-(3-chloropropyl)-1,3-dioxolane (6.62 g, 5.8 mL, 44.0 mmol) and triethylamine (12.5 mL, 90.0 mmol) in 2-butanone (250 mL) was heated to reflux and treated dropwise (1h) with a solution of NaI (3.0 g, 20.0 mmol) in 2-butanone (70 mL). The reaction mixture was refluxed for 12 h then treated dropwise (1 h) with a solution of NaI (3.0 g, 20.0 mmol) in 2-butanone (70 mL) and refluxed for another 12 h. After cooling at 23° C., the solvent was evaporated in vacuo leaving a residue which was solubilized in EtoAC (400 mL). The organic solution was washed with aqueous NaOH solution (20 mL, 2N); the aqueous phase was extracted with EtoAC (2×50 mL). The organic extracts were combined, dried ($MgSO_4$) and concentrated to dryness. The solution was chromatographed on a silica gel column (4.5×15 cm) using a mixture of 20% MeCN in EtoAc. Appropriate fractions were concentrated in vacuo leaving a pale yellow syrup which crystallized on standing, 10.5 g, mp 54°–55° C. (89%). Recrystallization from EtoAC-pet.ether mixture (1;14) gave an analytical sample, mp 55°–56° C.; $^1$HNMR (CDCl$_3$, 200 MHz) δ: 1.5–1.9 (m, 4H), 2.3–2.7 (m, 6H), 3.6–4.1 (m, 8H), 4.8–5.0 (m, 1H), 8.16 (s, 2H); IR (KBr) ν: 1610, 1555, 1489 cm$^{-1}$; UV (EtOH) λ: 244 (ε 17239), 332 (ε 1948);

Anal. Calcd. for C$_{14}$H$_{21}$N$_4$O$_2$F: C, 56.74; H, 7.14; N, 18.91. Found: C, 56.77; H, 7.15; N, 18.98.

Example 12

1-(2-Thienyl)-4-[4-(5-fluoro-2-pyrimidinyl)-1-piperazinyl]butanone

To a hot (78° C.) mixture of 4-(5-fluoro-2-pyrimidinyl) piperazine (4.00 g, 22.0 mmol), 4-chloro-2′-butyrothienone (3.57 mL, 22.0 mmol) and triethylamine (6.97 mL, 50.0 mmol) in methylethyl ketone (125 mL) was added dropwise (1 h) a solution of NaI (4.8 g, 32.0 mmol) in methylethyl ketone (125 mL). The resulting mixture was refluxed for 22 h, then cooled at 23° C. and concentrated to dryness in vacuo. The residue was diluted with CH$_2$Cl$_2$ (400 mL) and the solution washed with aqueous NaOH solution (0.5N, 44 mL). Aqueous phase was separated and extracted with CH$_2$Cl$_2$ (2×10 mL). Organic extracts were combined, dried (MgSO$_4$) and concentrated under reduced pressure to a crude material which was chromatographed on a silica gel column (5×16 cm) using a mixture 30–100% EtoAC in hexane. Appropriate fractions were combined and concentrated to afford a yellow solid, 2.0 g (27%). Recrystallization from Et$_2$O gave an analytical sample, mp 77°–8° C. $^1$H NMR (CDCl$_3$, 200 MHz) δ: 1.9–2.2 (m, CH$_2$CH$_2$CH$_2$, 2H), 2.3–2.7 (m, 6H), 2.96 (t, J=7.0 Hz, COCH$_2$, 2H), 3.6–3.9 (m, 4H), 7.0–7.2 (m, 1H), 7.5–7.7 (m, 1H), 7.7–7.8 (m, 1H), 8.18 (s, pyrimidinyl H, 2H); IR (KBr) ν: 1660, 1610, 1555, 1510, 1480, 1359 cm$^{-1}$; UV (EtOH) λ: 248 (ε 19699), 284 (ε 6287). 330 (ε 1816).

Anal. Calcd. for C$_{16}$H$_{19}$N$_4$OSF: C, 57.47; H, 5.73; N, 16.75; S, 9.59. Found: C, 57.42; H, 5.75; N, 16.81; S, 9.77.

Example 13

1-(4-Fluoronaphth-1-yl)-4-[4-(5-fluoro-2-pyrimidinyl)-1-piperazinyl]butanone (1) Ethyl 4-(4-(5-fluoropyrimidin-2-yl)piperazin-1-yl) butanoate A mixture of 4-(5-fluoro-2-pyrimidinyl)piperazine (1.37 g, 7.5 mmol), ethyl 4-bromobutanoate (1.07 mL, 7.5 mmol), triethylamine (1.35 mL, 9.7 mmol) in 2-butanone (50 mL) was refluxed under Ar atm. for 4 h. After cooling at 23° C., the reaction mixture was filtered and the filtrate concentrated under reduced pressure to a crude mixture which was dissolved in EtoAc (150 mL). The organic solution was washed with water (2×15 mL), dried (MgSO$_4$) and concentrated under reduced pressure to a crude mixture which was purified on a silica gel pad using a mixture 0–100% EtoAc in hexane as eluting solvent."Evaporation of appropriate fractions gave 1.66 g (75%) of pure compound; $^1$H NMR (CDCl$_3$, 200 MHz) δ: 1.25 (t, J=7.1 Hz, CH$_3$, 3H), 1.84 (t of t, J=7.1 Hz, H-3, 2H), 2.2–2.61 (m, 8H), 3.6–3.9 (m, 4H), 4.13 (q, J=7.1 Hz, CH$_2$CH$_3$, 2H), 8.17 (s, aromatic H, 2H); IR (film) ν: 1732 (C=O), 1610, 1552, 1500, 1360 cm$^{-1}$;

Anal. Calcd. for C$_{14}$H$_{21}$N$_4$O$_2$F: C, 56.74; H, 7.14; N, 18.91. Found: C, 56.63; H, 7.27; N, 18.66.

(2) Ethyl 2-(4-fluorobenzoyl)-4-(4-(5-fluoro-2-pyrimidinyl)piperazin-1-yl)butanoate To a cold (−78° C.) solution of lithium 1,1,1,3,3,3-hexamethyl disilazane in tetrahydrofuran (27.4 mL, 1N, 27.4 mmol) kept under Ar atm was added dropwise (10 min) a solution of ethyl 4-(4-(5-fluoro-2-pyrimidinyl)-piperazin-1-yl)butanoate (3.7 g, 12.5 mmol) in dry THF (12 mL). The reaction mixture was stirred 0.25 h at −78° C. and then treated dropwise (10 min) with a solution of 4-fluoro-1-naphthoyl chloride (2.6 g, 12.5 mmol) in dry THF (10 mL). The reaction was stirred −78° C. for 0.5 h then the cooling bath was removed. When the temperature of reaction mixture reached 0° C., HCl solution (40 mL, 0.3N) was added slowly followed by CH$_2$Cl$_2$ (350 mL); the organic phase was separated and aqueous phase was extracted with CH$_2$Cl$_2$ (120 mL). The organic extracts were combined, washed with water (2×45 mL) and brine, dried (MgSO$_4$) and concentrated under reduced pressure to a crude mixture which was purified on a silica gel pad (8.7×2.5 cm). Evaporation of appropriate fractions gave 2.8 g (48%) of the desired product compound which was recrystallized from EtOH to give an analytical sample; mp 95°–6° C.; $^1$H NMR (CDCl$_3$, 200 MHz) δ: 1.08 (t, J=7.1 Hz, CH$_3$, 3H), 2.1–2.7 (m, 8H), 3.5–3.8 (m, 4H), 3.9–4.3 (m, 2H), 4.5–4.7 (m, 1H), 7.1–7.25 (m, 1H), 7.5–7.8 (m, 2H), 8.17 (s), 8.0–8.02 (s and m, 4H), 8.6–8.7 (m, 1H); IR (KBr) ν: 1740 (C=O, 1682, 1630, 1611, 1600, 1578, 1554, 1510 cm$^{-1}$; UV (CH$_3$CN) λ: 224 (ε 43570), 242 (ε 37740), 304 (ε 9084);

Anal. Calcd. for C$_{25}$H$_{26}$N$_4$O$_3$F$_2$: C, 64.09; H, 5.59; N, 11.96. Found: C, 63.98; H, 5.62; N, 11.90. and 1.74 g (51%) of the by-product coupled compound: 1,7-bis [4-(5-fluoropyrimidin-2-yl)piperazin-1-yl]-3-ethoxycarbonylheptan-4-one. Treatment of an ethanolic solution of the oil with two equivalents of ethanolic HCl afforded the bis hydrochloride salt; mp 196°–8° C.;

(3) A mixture of Ethyl 2-(4-fluorobenzoyl)-4-(4-(5-fluoro-2-pyrimidinyl)piperazin-1-yl)butanoate (2.95 g, 6.3 mmol) in aqueous HCl (65 mL, 1N) was refluxed for 2 h, cooled at 23° C. and basified, first with aqueous NaOH solution (30 mL, 2N) and then with saturated NaHCO$_3$ solution until pH=9. The aqueous solution was extracted with CH$_2$Cl$_2$ (3×150 mL). Organic extracts were combined, washed with water (30 mL) and brine, dried (MgSO$_4$) and concentrated to dryness. The crude material was chromatographed on silica gel using a mixture of 50% CH$_2$Cl$_2$ in EtOAc. Appropriate fractions were combined and solvent evaporated under reduced pressure leaving 2.3 g (92%), mp 119°–120° C. Recrystallization from EtOH afforded analytical sample; mp 120°–1° C.; $^1$H NMR (CDCl$_3$, 200 MHz) δ: 2.03 (t, J=7.0 Hz, CH$_2$CH$_2$CH$_2$, 2H), 2.4–2.6 (m, 6H), 3H (t, J=7.0, CH$_2$CO, 2H), 3.8–3.9 (m, 4H), 7.1–7.2 (m, 1H), 7.5–7.8 (m, 2H), 7.9–8.0 m, 1H), 8.18 (s), 8.1–8.3 (m, 3H), 8.7–8.8 (m, 1H); IR (KBr) ν: 1681, 1630, 1611, 1600, 1575, 1555, 1494 cm$^{-1}$; UV (CH$_3$CN) λ: 226 (ε 40377), 298 (ε 7498);

Anal. Calcd. for C$_{22}$H$_{22}$N$_4$OF$_2$: C, 66.65; H, 5.59; N, 14.13. Found: C, 66.47; H, 5.59; N, 14.08.

Example 14

4-[5-(5-Fluoro-2-pyrimidinyl)-(1S,4S)-2,5-diazabicyclo[2.2.1]heptan-2-yl]-1-(4-fluorophenyl)butanone

A mixture of 2-(5-fluoro-2-pyrimidinyl)-(1S,4S)-2,5-diazabicyclo[2.2.1]heptane (Ex. 7(11)), 4-chloro-4'-fluorobutyrophenone ethylene ketal (3.53 g, 14.43 mmol), micropulverized $K_2CO_3$ (5.97 g, 43.29 mmol), and KI (0.36 g, 2.16 mmol) in 50 mL of MeCN was refluxed for 22 h. $K_2CO_3$ was filtered and the reaction mixture was concentrated in vacuo. 3N HCl (7 mL) was added to the residue. The reaction mixture was heated on a steam bath for 15 min. Then, 20 mL of EtOH was added and heating was continued for 30 min. The solution was concentrated and the residue was triturated with EtOH/Hexane which induced crystallization. The solid was collected by suction filtration to give the hydrochloride salt of the title compound (2.96 g, mp 192°-196° C. dec). The salt was converted to its free base to give the title compound (2.15 g, 41.6%).

Example 15

4-[5-(5-Fluoro-2-pyrimidinyl)-(1R,4R)-2,5-diazabicyclo[2.2.1]heptan-2-yl]-1-(4-fluorophenyl)butanone

The title compound was prepared as described for the 1S,4S isomer (Ex. 14). Yield: 2.40 g, 49.3%.

Example 16

4-[5-(5-Fluoro-2-pyrimidinyl)-(1S,4S)-2,5-diazabicyclo[2.2.1]heptan-2-yl]-1-(4-fluorophenyl)butanol hydrochloride

Into a solution of the ketone (Ex. 14) (2.15 g, 6.01 mmol) in 140 mL of EtOH was added $NaBH_4$ (0.68 g, 18.02 mmol). The reaction mixture was stirred at 23° C. for 2 h and refluxed for 0.5 h and concentrated in vacuo. The residue was taken up in $CH_2Cl_2$ (50 mL) and $H_2O$ (20 mL). The aqueous layer was made basic with 30% NaOH solution and extracted with $CH_2Cl_2$ (3×100 mL). Combined $CH_2Cl_2$ extracts were dried over $K_2CO_3$, filtered and concentrated under reduced pressure. Flash chromatography ($CH_2Cl_2$:MeOH; 93:7) gave the title compound (1.18 g, 54.6%). Conversion to the hydrochloride salt followed by recrystallization from EtOH-$Et_2O$ afforded a white solid, mp 186°-191° C.

Anal. Calc. for $C_{19}H_{22}F_2N_4O\cdot HCl$: C, 57.51; H, 5.85; N, 14.12. Found: C, 57.35; H, 5.89; N, 14.10.

Example 17

4-[5-(5-Fluoro-2-pyrimidinyl)-(1R,4R)-2,5-diazabicyclo[2.2.1]heptan-2-yl]-1-(4-fluorophenyl)butanol hydrochloride

The title compound was prepared as described for the 1S,4S isomer (Ex. 16). Yield: 1.17 g (48.5%), mp 187°-191° C.

Anal. Calc. for $C_{19}H_{22}F_2N_4O\cdot HCl$: C, 57.51; H, 5.85; N, 14.12. Found: C, 57.46; H, 5.89; N, 14.21.

Formula 1B Compounds

Example 18

1-[4-Acetamido-4-(4-fluorophenyl)butyl]-4-(5-fluoro-2-pyrimidinyl)piperazine monohydrochloride

(1)

1-[4azido-4-(4-fluorophenyl)butyl]-4-(5-fluoro-2-pyrimidinyl)piperazine monohydrochloride To a cold (5° C.) solution of triphenylphosphine (12.6 g, 48.0 mmol) in dry THF (130 mL) kept under an Ar atmosphere was added dropwise over 1 h period diisopropyl azodicarboxylate (9.5 mL, 48.2 mmol) followed by a solution of 1-(4-fluorophenyl)-4-[4-(5-fluoro-2-pyrimidinyl)-1-piperazinyl] butanol-1-01 Ex. 5; (14.6 g, 41.9 mmol) in dry THF (275 mL). The reaction mixture was immediately treated dropwise (10 min) with a solution of diphenylphosphoryl azide (13.3 g, 48.3 mmol) in dry THF (130 mL). The resulting reaction mixture was stirred at 5° C. for 1 h then at 23° C. for 16 h before being concentrated to dryness. The residue was suspended in $CH_2Cl_2$ (200 mL) and filtered. The filtrate was concentrated and chromatographed on a silica gel pad using a mixture 30-100% EtOAc in $CH_2C_2$ as eluting solvent. Appropriate fractions were concentrated under reduced pressure leaving 8.0 g, 51%; $^1H$ NMR ($CDCl_3$, 200 MHz) δ: 1.3–2.0 (m, 4H), 2.2–2.6 (m, 6H), 3.6–3.9 (m, 4H), 4.43 (t, J=7.1 Hz, 1H), 6.9–7.1 (m, 2H), 7.1–7.4 (m, 2H), 8.16 (s, 2H). A part of the compound was converted to monohydrochloride salt and recrystallized from EtOH-$Et_2O$ mixture to afford an analytical sample, mp 176°-8° C.; $^1H$ NMR (DMSO-d6, 200 MHz) δ: 1.5–2.0 (m, 4H), 2.8–3.2 (m, 4H), 3.2–3.6 (m, 4H), 4.4–4.7 (m, 2H), 4.7–4.9 (m, 1H), 7.2–7.4 (m, 2H), 7.4–7.6 (m, 2H), 8.5 (s, 2H), 10.5–10.9 (m, 1H); IR (KBr) ν: 2810–2300, 2100, 1605, 1560, 1510, 1475, 1440 cm$^{-1}$; UV ($H_2O$) λ: 238 (ε 16600), 320 (ε 2011);

Anal. Calcd. for $C_{18}H_{21}N_7F_2\cdot HCl\cdot 0.15\ H_2O$: C, 52.40; H, 5.45; N, 23.76. Found: C, 52.58; H, 5.34; N, 23.88.

(2)

1-(4-fluorophenyl)-4-(5-fluoro-2-pyrimidinyl)-1-piperazinylbutanamine

A mixture of 1-[4-azido-4-(4-fluorophenyl)butyl]-4-(5-fluoro-2-pyrimidinyl)piperazine (3.3 g, 8.84 mmol), 10% palladium on charcoal (0.33 g) in EtOH (70 mL) was hydrogenated under 40 psi at 23° C. for 2 h. The mixture was filtered and solvent concentrated in vacuo leaving the title compound, 2.93 g (95%); IR (film) ν: 1610, 1552, 1505 cm$^{-1}$.

(3) To a cold (5° C.) solution of 1-(4-fluorophenyl)-4-(5-fluoro-2-pyrimidinyl)-1-piperazinylbutanamine (2.33 g, 6.7 mmol) in glacial AcOH (10 mL) was added dropwise (20 min) acetic anhydride (0.64 mL, 6.8 mmol). The cooling bath was removed and the reaction mixture was stirred at 23° C. for 16 h, concentrated to half of its initial volume and diluted in $CH_2Cl_2$ (100 mL). The organic solution was basified with the addition of saturated $NaHCO_3$ aqueous solution until pH 9. The organic layer was separated and the aqueous layer was extracted with $CH_2Cl_2$ (2×50 mL). Organic layers were washed with brine, dried ($MgSO_4$) and concentrated to dryness. The resulting residue was chromatographed on a silica gel pad (8.7×4.5 m) using a mixture of 5–20% EtOH in $CHCl_3$. Appropriate fractions were concentrated in vacuo leaving a solid, 2.0 g (77%).

Recrystallization from EtOH-Et$_2$O mixture gave an analytical sample, mp 142°-3° C.; $^1$H NMR (CDCl$_3$, 200 MHz) δ: 1.3-1.7 (m, 2H), 1.7-1.9 (m, 2H), 1.99 (s, NHCOCH$_3$, 3H), 2.3-2.6 (m, 6H), 3.7-3.9 (m, 4H), 4.9-5.1 (m, CHNH, 1H), 6.14 (bd, J=6.7 Hz, CHNH, 1H), 6.9-7.1 (m, 2H), 7.1-7 3 (m, 2H), 8.18 (s, pyrimidinyl H, 2H); IR (KBr) ν: 3290, 1650, 1610, 1551, 1510, 1500, 1395, 1356 cm$^{-1}$; UV (CH$_3$CH) λ: 246 (ε 19523), 332 (ε 1981);

Anal. Calcd. for C$_{20}$H$_{25}$NOF$_2$: C, 61.68; H, 6.47; N, 17.98. Found: C, 61.82; H, 6.54; N, 18.02.

Example 19

1-[4-(4-Fluorobenzamido)-4-(4-fluorophenyl)butyl]-4-(5-fluoro-2-pyrimidinyl)piperazine To a cold (5° C.) solution of 1-(4-fluorophenyl)4-(5-fluoro-2-pyrimidinyl)-1-piperazinylbutanamine (1.93 g, 5.55 mmol) in CH$_2$Cl$_2$ (40 mL) was added triethylamine (0.78 mL, 5.6 mmol) and 4-fluorobenzoyl chloride (0.66 mL, 5.6 mmol) over 30 min period. The reaction mixture was stirred at 5° C. for 1 h then at 23° C. for 1 h before being diluted with CH$_2$Cl$_2$ chloride (100 mL). The resulting organic solution was washed with cold (0° C.) water (20 mL), aqueous NaHCO$_3$ saturated solution (pH 9) and brine, dried (MgSO$_4$) and concentrated to dryness. The crude mixture was chromatographed on a silica gel pad using a mixture of 4-10% EtOH in CH$_2$Cl$_2$. Appropriate fractions were concentrated to afford a white solid, 2.0 g (77%). Analytical sample was prepared from recrystallization from EtOH, mp 147°-8° C.; $^1$H NMR (CDCl$_3$, 200 MHz) δ: 1.4-1.8 (m, 2H), 1.8-2.2 (m, 2H), 2.3-2.6 (m, 6H), 3.6-3.9 (m, 4H), 5.0-5.3 (m, CH$_2$CHNH, 1H), 6.6 (d, J=7.3 Hz, CHNH, 1H), 6.9≅7.2 (m, 4H), 7.26-7.4 (m, 2H), 7.7-7.9 (m, 2H), 8.18 (s, pyrimidinyl H, 2H); IR (KBr) ν: 3330, 1632, 1605, 1552, 1505, 1395, 1358 cm$^{-1}$; UV (CH$_3$CN) λ: 244 (ε 25182), 332 (ε 1922);

Anal. Calcd. for C$_{25}$H$_{26}$N$_5$OF$_3$: C, 63.96; H, 5.58; N, 14.92. Found: C, 64.07; H, 5.59; N, 14.90.

Example 20

1-[4-(4-Fluorophenyl)-4-(4-fluorophenylsulfonamido)butyl]-4-(5-fluoro-2-pyrimidinyl)piperazine To a cold (5° C.) solution of 1-(4-fluorophenyl)-4-(5-fluoro-2-pyrimidinyl)-1-piperazinylbutanamine (2.34 g, 6.73 mmol) in CH$_2$Cl$_2$ (30 mL) was added triethylamine (0.94 mL, 6.7 mmol) and a solution of 4-fluorobenzene sulfonyl chloride (1.31 g, 6.73 mmol) in CH$_2$Cl$_2$ (15 mL) over 0.5 h. The reaction mixture was stirred at 5° C. for 1 h then at 25° C. for 1 h before being diluted with CH$_2$Cl$_2$ (160 mL). The resulting organic solution was washed with cold water (0° C.) (2×20 mL), aqueous NaHCO$_3$ saturated solution (pH 9) and brine, dried (MgSO$_4$) and concentrated to dryness. The crude material was chromatographed on a silica gel pad using a mixture of 5-10% EtOH in CH$_2$Cl$_2$. The appropriate fractions were concentrated in vacuo leaving a white solid, 2.8 g (82%). Recrystallization from EtOH afforded an analytical sample, mp 128°-9° C; $^1$H NMR (CDCl$_3$, 200 MHz) δ: 1.3-1.7 (m, 2H), 1.7-1.9 (m, 1H), 1.9-2.1 (m, 1H), 2.2-2.8 (m, 6H), 3.6-4.2 (m, 4H), 4.48 (bs, 1H), 6.8-7.2 (m, 6H), 7.5-7.8 (m, 2H), 8.20 (s, pyrimidinyl H, 2H), 8.58 (bs, NH, 1H); IR (KBr) ν: 3270, 1610, 1592, 1554, 1509, 1492, 1439, 1400 cm$^{-1}$; UV (CH$_3$CN) λ: 244 (ε 19445), 330 (ε 1915);

Anal. Calcd. for C$_{24}$H$_{26}$N$_5$O$_2$F$_3$S: C, 57.02; H, 5.18; N, 13.85; S, 6.34. Found: C, 56.89; H, 5.23; N, 13.87; S, 6.58.

Example 21

1-[3-(4-Fluorophenylsulfonyl)propyl]-4-(5-fluoro-2-pyrimidinyl)piperazine

To a cold (5° C.) solution of 1-[3-(4-fluorophenylthio)propyl]-4-(5-fluoro-2-pyrimidinyl)piprazine (3.55 g, 10.1 mmol) in acetic acid (6 mL) was added ammonium molybdate (0.08 g, 0.4 mmol) and 30% H$_2$O$_2$ solution (2.8 mL, 27.4 mmol) was added dropwise at such a rate that the temperature was kept at 10° C. (~3 h). The reaction mixture was then stirred at 23° C. for 16 h before being diluted with water (120 mL) and CH$_2$Cl$_2$ (200 mL). Excess was destroyed by addition of aqueous saturated sodium sulfite solution. The mixture was basified with Na$_2$CO$_3$ (pH 8.5). The organic phase was separated and the aqueous phase further extracted with CH$_2$Cl$_2$ (2×100 mL). The organic extracts were combined, washed with brine, dried (MgSO$_4$) and concentrated under reduced pressure leaving a crude mixture which was purified on a silica gel pad using a mixture of 2% EtOH in CHCl$_3$ as eluting solvent. The appropriate fractions were concentrated in vacuo leaving a white solid 3.6 g, 93% which was recrystallized from EtOH giving an analytical sample; mp 132.5-3.5° C., $^1$H NMR (CDCl$_3$, 200 MHz) δ:1.8-2.0 (m, 2H), 2.3-2.6 (m, 6H), 3.1-3.3 (m, 2H), 3.6-3.8 (m, 4H), 7.1-7.3 (m, 2H), 7.8-8.0 (m, 2H), 8.16 (s, 2H); IR (KBr) ν: 1612, 1590, 1558, 1491, 1470, 1450, 1358 (SO$_2$), 1145 (SO$_2$) cm$^{-1}$; UV (CH$_3$CN) λ: 218 (ε 12429), 246 (ε 17791), 330.

Example 22

1-Cyclohexyl-4-[4-(5-fluoro-2-pyrimidinyl)-1-piperazinyl]butanol (1) 4-[4-(5-fluoro-2-pyrimidinyl)-1-piperazinyl] butyraldehyde A mixture of 4-(4-(5-fluoro-2-pyrimidinyl)piperazin-1-yl)) butyraldehyde ethylene acetal (1.36 g, 4.6 mmol) and aqueous HCl (6N, 8 mL, 48.0 mmol) was stirred at 45° C. for 2 h and then basified after cooling with aqueous NaOH solution (2N, 22-24 mL, ~pH 10). The resulting mixture was extracted with CH$_2$Cl$_2$ (3×50 mL) leaving 1.3 g of crude oil after evaporation of solvent. Purification on a silica gel column (2.5×10 cm) using a mixture of 20% MeCN in EtOAc afforded 0.86 g (74%) of pale yellow syrup; $^1$H NMR (CDCl$_3$, 200 MHz) δ: 1.86 (m, 2H), 2.39 (t, J=6.9 Hz), 2.3-2.6 (t, m, 8H), 3.74 (m, 4H), 8.18 (s, 2H), 9.8 (t, J=1.6 Hz, 1H).

(2) To a cold (−30° C.) solution of 4-(4-(5-fluoropyrimidinyl)-piperazin-1-yl)) butyraldehyde (4.32 g, 17.1 mmol) in THF kept under N$_2$ atmosphere was added dropwise (0.5 h) a solution of cyclohexyl magnesium chloride in Et$_2$O (17 mL, 2N, 34.0 mmol). The reaction mixture was stirred at −30° C. for 1 h before adding water dropwise (35 mL) and EtOAc (350 mL). The organic phase was separated and the aqueous phase extracted with EtOAc (200 mL). The organic extracts were dried (MgSO$_4$) and concentrated under reduced pressure to a yellow syrup (6.1 g). Purification on silica gel column (4.5×17 cm) gave 2.54 g (44%) of a colorless syrup which crystallized (mp 80°-2° C.) on standing. Recrystallization from EtOAc - pet. ether mixture afforded an analytical sample; mp 81°-3° C.; $^1$H NMR (CDCl$_3$, 200 MHz) δ: 0.8-1.5 (m, 8H), 1.5-2.0 (m, 7H), 2.3–2.7 (m, 6H), 3.2–3.4 (m, 1H), 3.7–4.0 (m, 4H), 8.18 (s, 2H); IR (KBr) ν: 3600–3100, 1610, 1555, 1510 cm$^{-1}$; UV (EtOH) λ: 244 (ε 19076), 330 (ε1973);

Anal. Calcd. for $C_{18}H_{29}N_4OF \cdot O \cdot 2H_2O$: C, 63.58; H, 8.71; N, 16.48. Found: C, 63.84; H, 8.71; N, 16.51.

Example 23

1-(4-Fluoronaphth-1-yl)-4-[4-(5-fluoro-2-pyrimidinyl)-1-piperazinyl]butanol

A solution of 1-(4-fluoronaphth-1-yl)-4-(5-fluoro-2-pyrimidinyl)piperazine (20 g, 5.0 mmol) in THF (20 mL) was treated with a solution of NaBH$_4$ (0.094 g, 2.5 mmol) in EtOH (20 mL) and stirred at 23° C. for 2 h. The reaction mixture was acidified to pH 1 with aqueous HCl solution (13 mL, 1N) then basified with aqueous NaOH solution (20%) to pH 9 and diluted with EtOAc (400 mL). The resulting mixture was washed with water (2×20 mL) and brine, dried (MgSO$_4$) and concentrated in vacuo to a crude material which was chromatographed on a silica gel pad (6.7×3 cm) using a mixture of 0–100% EtOAc in CH$_2$Cl$_2$. Evaporation of appropriate fractions gave 1.92 g (96%) of title compound. Recrystallization from EtOH gave an analytical sample, m.p. 129°–31° C.; $^1$H NMR (CDCl$_3$, 200 MHz) δ: 1.7–2.0 (m, 3H), 2.1–2.4 (m, 1H), 2.4–2.7 (m, 4H), 2.7–2.9 (m, 2H), 3.8–4.0 (m, 4H), 5.3–5.5 (m, 1H), 7.1–7.2 (m, 1H), 7.19 (s, OH, 1H), 7.4–7.8 (m, 3H), 8.0–8.3 (m, 4H), 8.2 (s); IR (KBr) ν: 3600–3310, 3300–3000, 1635, 1610, 1604, 1585, 1555, 1495 cm$^{-1}$; UV (CH$_3$CN) λ: 226 (ε 35991), 246 (ε 15791), 288 (ε 4801);

Anal. Calcd. for $C_{22}H_{24}N_4OF_2$: C, 66.32; H, 6.07; N, 14.06. Found: C, 66.44; H, 6.09; N, 13.77.

Example 24

α-(4-Fluorophenyl)-4-(5-fluoro-2-pyrimidinyl)-1-piperazine pentanenitrile hydrochloride To a mixture of potassium t-butoxide (5.28 g, 0.042 mole in 1,2-dimethoxyethane (45 mL) cooled to −4° C. was added dropwise over the course of 0.5 h a solution of 1-(4-fluorophenyl)-4-(5-fluoro-2-pyrimidinyl)-1-piperazinebutan-1-one (6.21 g, 0.018 mole) and tosylmethylisocyanide (4.68 g, 0.024 mole) in 1,2-dimethoxyethane (75 mL) and EtOH (1.8 mL). After completion of addition, the mixture was stirred at 25° C. for 0.5 h then heated at 45° C. for 18 h. The reaction mixture was filtered, the filtrate concentrated in vacuo and the residue dissolved in EtOAc and flash-chromatographed on silica gel using EtOAc as eluant. Appropriate fractions were combined and concentrated in vacuo to afford 2.2 g (34%) of the product free base. The base was dissolved in EtOH (25 mL) and treated with ethanolic HCl to obtain the hydrochloride salt which was collected by filtration and dried affording 1.88 g, mp 234°–236° C.

By following substantially the procedures described above in the description of the invention and in the above actual examples, additional Formula I compounds may be prepared. Some additional Formula I compounds are listed in Table 1.

Example 25

Anoxic Nitrogen Test in Rats

The animals utilized are male Sprague-Dawley rats (200–240 grams) housed four animals per cage in a normal controlled environment with unlimited access to food and water. Usually there are 8 animals per dose, however, 4 animals can be employed to obtain an initial impression of a compound's activity. Animals surviving the anoxic insult are sacrificed via CO$_2$ inhalation following completion of the observation session (2 hr).

Method

Animals are parenterally or orally administered the vehicle or test compound 30 minutes prior to the anoxic insult. The anoxic episode consists of placing up to 4 animals in the sealed test chamber (10" l × 10" w × 6" h) continuously flushed with pure N$_2$ (4.5 grade) at a flow rate of 3 SCFM for 1 min. Animals are then promptly removed to normal atmosphere and observed for the 2 hour time period. Typically, animals become disoriented within 15 sec which leads into convulsions at 30 to 35 sec after which they remain motionless.

In spite of the fact that after the N$_2$ exposure the heart is still beating, all control animals fail to gasp when removed from the chamber and usually expire within 3 minutes. Drug treated animals, however, still gasp or start gasping after being removed which is a good indication if an animal will survive the N$_2$ exposure (1). Results are recorded as:

$$\frac{\text{Number of animals surviving (2 hr)}}{\text{Number of animals tested}}$$

and are statistically evaluated using the Finney Dose Response program for determination of the ED$_{50}$ and its corresponding 95% confidence limits.

| | DRUG EXAMPLE | | | | | |
|---|---|---|---|---|---|---|
| | # SURVIVING/# TESTED | | | | | |
| | Dose mg/kg, ip | | | | | ED$_{50}$ (19/20 C.L.) |
| Sabeluzole | 5.0 / 3/8 | 10 / 15/16 | 20 / 18/20 | | | 4.7 (0.2–7.6) |
| (+)MK-801 | 0.5 / 0/8 | 1.0 / 8/24 | 2.0 / 8/24 | 4.0 / 8/16 | 10 / 7/8 | 3.1 (2.0–6.9) |

REFERENCES

1. Wauquier, A. et al: Arch. Int. Pharmacodyn., 249: 330–334 (1981).
2. Wauquier, A. et al; Drug Dev. Res., 8: 373–380 (1986)

Compounds of the present invention were rated at each dose level tested using the following rating scale:

I = inactive (0% survival)
+ = weak activity (up to 25% survival)
+ + = moderate activity (25–50% survival)
+ + + = good activity (51–75% survival)
+ + + + = very good activity (76–100%)

Table 2 contains test data for representative Formula I compounds. The highest rated dose level is the one displayed in Table 2.

TABLE 1
Additional Formula I Compounds
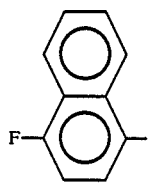
| No. | Z | X | n | m | R¹ | R² | R³ |
|-----|---|---|---|---|----|----|----|
| 26. | 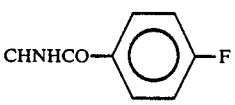 | 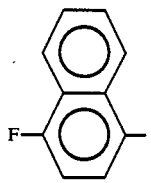 | 3 | 0 | H | F | H |
| 27. | 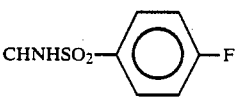 | 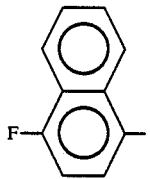 | 3 | 0 | H | Cl | H |
| 28. | 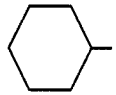 | CH₂ | 3 | 0 | H | F | H |
| 29. | 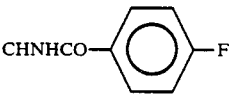 | 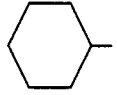 | 3 | 0 | H | Br | H |
| 30. | 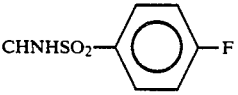 | 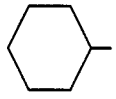 | 3 | 0 | H | F | H |
| 31. | 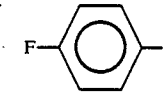 | CH₂ | 3 | 0 | H | F | H |
| 32. | 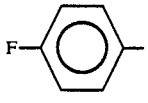 | CHOH | 3 | 0 | CH₃ | F | H |
| 33. | 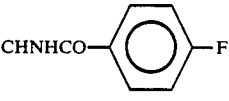 | 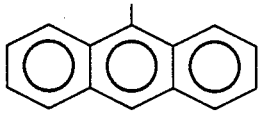 | 3 | 0 | H | F | H |
| 34. | (anthracenyl) | CH₂ | 3 | 0 | H | F | H |

TABLE 1-continued

Additional Formula I Compounds

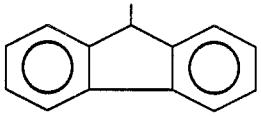

| No. | Z | X | n | m | R¹ | R² | R³ |
|-----|---|---|---|---|----|----|----|
| 35. | | $CH_2$ | 3 | 0 | H | F | H |
| 36. | | CHOH | 2 | 1 | H | F | H |

TABLE 2

| Ex. No. | Dose (mg/kg ip) | Rating |
|---------|-----------------|--------|
|         | 40              | ++     |
| 40      | +               |        |
| 9       | 40              | +++    |
| 40      | +               |        |
| 10      | 40a             | +      |
| 11      | 40              | +      |
| 21      | 40              | +      |
| 18      | 40              | +      |
| 19      | 40              | ++++   |
| 22      | 80              | +++    |
| 20      | 80              | ++++   |
| 23      | 100             | ++++   |
| 13      | 40              | ++     |
| 80      | ++++            |        |
| 12      | 40              | +      |

*a given 60 minutes prior to anoxia testing.*

Additional Detailed Description of The Invention

Some additional compounds related to Formula I have been prepared and found to have the useful anti-ischemic properties of the previous compounds of Formula I. These additional compounds extend the structural description of the X moiety in Formula I to give Formula I' which is the same as Formula I except for X.

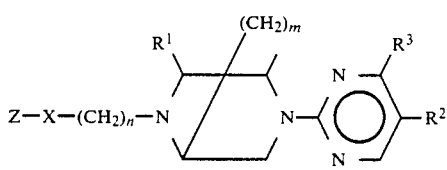

Group X is now defined as a member selected from the group consisting of —O—; —S—; —SO₂—; —CO—;

$$-CR^4-\begin{matrix}OR^7\\ \end{matrix}$$

wherein $R^4$ is hydrogen or $C_{1-6}$ alkyl and $R^7$ is hydrogen, $C_{1-6}$ alkyl, $C_{2-7}$ alkanoyl or

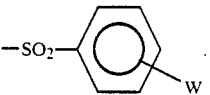

wherein W is hydrogen, halogen or alkoxy; and —CH-$R^5$— wherein $R^5$ is hydrogen, CN, $N_3$ or $NHR^6$ with $R^6$ being $R^7$ or $$-SO_2-\!\!\!\bigcirc\!\!\!-W$$

By $C_{1-6}$ alkyl (for $R^4$), it is intended that both linear alkyl and cyclo alkyl moieties are included. By $C_{2-7}$ alkanoyl is intended alkylcarbonyl groups such as acetyl, propanoyl, cyclohexanoyl and the like.

These additional compounds were prepared by employing the general synthetic processes described hereinabove, using alterations which would be apparent to a skilled chemist in order to produce the desired product compound. Some additional examples are provided hereinbelow as guidance for synthesis of Formula I' compounds where X has been extended in structural definition.

Compounds of Formula I'

Example 37

1-Cyclohexyl-1-(4-fluorophenyl)-4-(4-(5-fluoro-2-pyrimidinyl)-1-piperazinyl)-1-butanol A cold (15° C.) solution of 1-(4-fluorophenyl)-4-(4-(5-fluoro-2-pyrimidinyl)-1-piperazinyl)-1-butanone (2.1 g, 6.1 mmol) in dry tetrahydrofuran (25 mL) kept under argon atmosphere was treated dropwise (15 min) with a solution of cyclohexylmagnesium chloride in ether (2.0M, 3.18 mL, 6.36 mmol). The cooling bath was removed and reaction mixture after being stirred at 23° C. for 2 h was treated dropwise (15 min) with HCl (2N, 3.5 mL), stirred for 15 min and diluted with CHCl₃ (50 mL). The organic phase was basified with NaHCO₃ and separated. Aqueous phase was extracted with CHCl₃ (15 mL). The organic extracts were dried (MgSO₄) and concentrated in vacuo to a sticky solid which was purified on silica gel column using a mixture of 40–100% AcOEt in CHCl$_3$ as eluting solvent. The first group of fractions was concentrated in vacuo to give the carbinol as a solid, 1.1 g, 42%. The second group of fractions gave, after evaporation of solvent, the initial ketone 1.0 g, 48%. The carbinol was recrystallized from EtOH to give an analytical sample, mp 53°–9° C.

Anal. Calcd. for C$_{24}$H$_{32}$F$_2$N$_4$O 0.25 C$_2$H$_6$O: C, 66.57; H, 7.64; N, 12.67. Found: C, 66.37; H, 7.56; N, 12.53.

Anti-ischemic Rating +++ at 40 mg/kg ip.

Example 38

1-(4-Fluorophenyl)-4-(4-(5-fluoro-2-pyrimidinvl)-1-piperazinyl)-1-butyl acetate

A cold (5° C.) mixture of 1-(4-fluorophenyl)-4-(4-(5-fluoro-2-pyrimidinyl)-1-piperazinyl)-1-butanol monohydrochloride[1] (3.0 g, 7.8 mmol) and Et$_3$N (2.38 mL, 17.1 mmol) in CH$_2$Cl$_2$ (55 mL) was treated dropwise (10 min) with AcCl (0.67 mL, 9.4 mmol). The reaction mixture was stirred at 5° C. for 0.25 h and then at 23° C. for 2 h before being diluted with CH$_2$Cl$_2$ (250 mL). The organic solution was washed with water (30 mL), saturated Na$_2$CO$_3$ solution to bring pH to 9, water (20 mL) and brine, dried (MgSO$_4$) and concentrated in vacuo to a solid which was purified on silica gel column using a mixture of 30–40% AcOEt in CH$_2$Cl$_2$. The appropriate fractions were collected and concentrated in vacuo to a white solid, 2.93 g, 96%. Recrystallization from ether-hexane mixture afforded analytical sample, mp 76°–7° C.
1. See U.S. Pat. No. 4,605,655 for preparation and properties.

Anal. Calcd. for C$_{20}$H$_{24}$F$_2$N$_4$O$_2$: C, 61.53; H, 6.20; N, 14.35. Found: C, 61.55; H, 6.19; N, 14.33.

Example 39

1-(4-Fluorophenyl)-4-(4-(5-fluoro-2-pyrimidinyl)-1-piperazinyl)-1-butyl 4-fluorobenzoate hydrochloride A cold (5° C.) mixture of 1-(4-fluorophenyl)-4-(4-(5-fluoro-2-pyrimidinyl)-1-piperazinyl)-1-butanol monohydrochloride. (3.0 g, 7.8 mmol) and Et$_3$N (2.40 mL, 17.2 mmol) in CH$_2$Cl$_2$ (55 mL) was treated dropwise (10 min) with 4-fluorobenzoyl chloride (1.11 mL, 9.4 mmol). The cooling bath was removed and the reaction mixture stirred at 23° C. for 20 h before being diluted with CH$_2$Cl$_2$ (250 mL). The organic solution was washed with water (30 mL), saturated Na$_2$CO$_3$ solution to bring pH to 9, water (30 mL) and brine, dried (MgSO$_4$) and concentrated in vacuo to a crude mixture which was purified on silica gel column using a mixture of 20–30% AcOEt in CH$_2$Cl$_2$. The appropriate fractions were concentrated in vacuo to a thick syrup, 3.4 g, 93%. The free base was solubilized in EtOH and treated with HCl in EtOH (one equivalent). The solvent was removed under reduced pressure leaving a gum which was crystallized from AcOEt affording analytical sample mp 94°–8° C.

Anal. Calcd. for C$_{25}$H$_{25}$F$_3$N$_4$O$_2$ 1.15 HCl: C, 58.60; H, 5.14; N, 10.93; Cl, 7.96. Found: C, 58.87; H, 5.17; N, 10.89; Cl, 7.94.

Anti-ischemic rating +++ at 40 mg/kg ip.

Example 40

1-(4-Azido-4-(4-fluoro-1-naphthyl)-1-butyl)-4-(5-fluoro-2-pyrimidinyl)piperazine monohydrochloride To a cold (5° C.) solution of Ph$_3$P (6.93 g, 26.4 mmol) in dry tetrahydrofuran (70 mL) kept under argon atmosphere was added dropwise (1 h) diisopropyl azodicarboxylate (5.2 mL, 26.4 mmol) and a solution of 1-(4-fluoro-1-naphthyl)-4-(4-(5-fluoro-2-pyrimidinyl)-1-piperazinyl)-1-butanol[1] (9.2 g, 23.1 mmol) in dry tetrahydrofuran (140 mL), followed by the addition of a solution of diphenylphosphoryl azide (7.27 g, 26.4 mmol) in dry tetrahydrofuran (70 mL) over 10 min period. The reaction mixture was stirred at 5° C. for 1 h then at 23° C. for 2 h before being filtered. The cake was triturated several times in CH$_2$Cl$_2$ and filtered. All the filtrates were combined and concentrated in vacuo to a thick yellowish gum which was purified on silica gel column using a mixture of 0–30% AcOEt in CH$_2$Cl$_2$. The appropriate fractions were concentrated in vacuo leaving a colorless gum, 3.4 g, 35%. A solution of the free base in EtOH was treated with one equiv. of HCl in EtOH. The solution was concentrated in vacuo; the solid was crystallized from EtOH to give analytical sample, mp 212°–3° C. dec.
1. See Example 23 for synthesis.

Anal. Calcd. for C$_{22}$H$_{23}$F$_2$N$_7$ HCl: C, 57.45; H, 5.26, N, 21.32. Found: C, 57.25; H, 5.05; N, 21.10.

Anti-ischemic rating ++ at 40 mg/kg ip.

Example 41

1-(4-Fluoro-1-naphthyl)-4-(4-(5-fluoro-2-pyrimidinyl)-1-piperazinyl) butylamine hydrochloride A mixture of 1-(4-azido-4-(4-fluoro-1-naphthyl)-1-butyl)-4-(5-fluoro-2-pyrimidinyl)piperazine[1] (0.79 g, 1.87 mmol) and 10% Pd/C (0.08 g) in EtOH (17 mL) was hydrogenated at 23° C. for 3 h under 40 psi and then filtered. The filtrate was concentrated in vacuo to a gum which was purified on silica gel column using a mixture of 0–10% MeOH in CH$_2$Cl$_2$. The appropriate fractions were concentrated in vacuo giving a white solid; 0.50 g, 68%. A solution of the free base in EtOH was treated with HCl in EtOH (1 equiv); on standing. the HCl salt crystallized out; mp 228°–30° C. dec.
1. See Example 40.

Anal. Calcd. for C$_{22}$H$_{27}$F$_2$N$_5$ 1.2 HCl: C, 59.89; H. 5.98; N, 14.87; Cl, 9.64. Found: C, 59.95; H, 5.94; N, 15.75; Cl, 9.66.

Anti-ischemic rating ++++ at 40 mg/kg ip.

Example 42

1-[4-(4-Fluorophenyl)-4-methoxybutyl]-4-(5-fluoropyrimidin-2-yl) piperazine hydrochloride A mixture of 1-(4-fluorophenyl)-4-(4-(5-fluoro-2-pyrimidinyl)-1-piperazinyl)-1-butanol (4.79 g, 13.7 mmol) and sodium hydride (0.34 g, 14.2 mmol) in dry tetrahydrofuran was refluxed for 4 h under argon atmosphere before being cooled at 10° C. and treated with MeI (0.85 mL, 1.37 mmol). The reaction mixture was stirred at 25° C. for 24 h and diluted with CH$_2$Cl$_2$ (200 mL) and water (40 mL). The organic phase was separated and aqueous phase extracted with CH$_2$Cl$_2$ (10 mL). The organic extracts were dried (MgSO$_4$) and concentrated in vacuo to a crude mixture which was triturated in hexane and filtered. The filtrate was concentrated in vacuo and purified on silica gel column using AcOEt as eluting solvent. The appropriate fractions were concentrated in vacuo to a syrup, 3.3 g, 66%. The free base was solubilized in EtOH and resulting solution was treated with HCl (1.2M, 1.2 equiv.) in EtOH. The solution was concentrated to dryness and the solid was recrystallized from EtOH; mp 199°–201° C.

Anal. Calcd. for $C_{19}H_{24}N_4OF_2$ 1.0 HCl: C, 57.21; H, 6.32; N, 14.05. Found: C, 57.22; H, 6.32; N, 13.97.

Anti-ischemic rating ++ at 40 mg/kg ip.

Additional Formula I' compounds are displayed in Table 3.

TABLE 3

Additional Formula I' Compounds

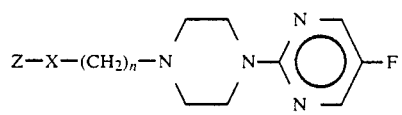

$$Z-X-(CH_2)_n-N\underset{\phantom{N}}{\overset{\phantom{N}}{\diagup\!\!\!\diagdown}}N-\text{pyrimidinyl-F}$$

| No. | Z | X | n | Yield % | MP (°C.) | Anti-ischemic Rating |
|---|---|---|---|---|---|---|
| 26 | F-naphthyl | CHNHCO-C6H4-F | 3 | 79 | 133–135 | ++ |
| 28 | F-naphthyl | CH2 | 3 | 86 | 75–76 | +++ |
| 30 | cyclohexyl-CH2 | CHNHSO2-C6H4-F | 3 | 63 | 123–125 | ++ |
| 31 | cyclohexyl | CH2 | 3 | 32 | 72–73 | ++ |
| 43 | F-C6H4 | CHNHCOPh | 3 | 77 | 165–166 | ++ |
| 44 | F-C6H4 | CHNHCO-naphthyl-F | 3 | 82 | 178–179 | ++ |
| 45 | F-naphthyl | CHNHSO2-C6H4-F | 3 | 76 | 130–131 | + |
| 46 | F-C6H4 | CHO2CPh | 3 | 92 | 159–160* | ++ |

TABLE 3-continued

Additional Formula I' Compounds

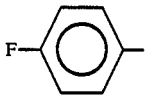

| No. | Z | X | n | Yield % | MP (°C.) | Anti-ischemic Rating |
|---|---|---|---|---|---|---|
| 47 | 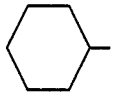 | CH$_2$ | 1 | 78 | 85–86 | + |
| 48 |  | C=O | 3 | 43 | 68–69 | ++++ |
| 49 | 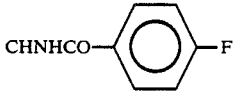 | CHNHCO–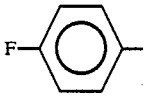–F | 3 | 17 | 142–144 | + |
| 50 | F– | CHNHCO– | 3 | 93 | 165–166 | – |
| 51 | 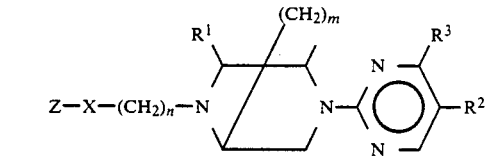 | CHNH$_2$ | 3 | 52 | 277–8B* | – |

(1) Test compound given at a dose of 40 mg/kg i.p. 60 minutes prior to anoxia testing.
*Mp of hydrochloride salt

We claim:
I' A compound of Formula I' and its pharmaceutically

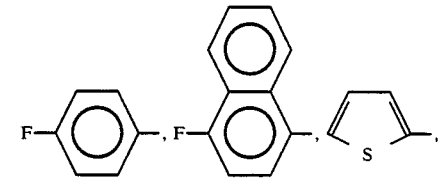

acceptable acid addition salts and/or solvates thereof wherein

Z is a member selected from the group consisting of naphthalenyl, anthracenyl, fluorenyl, phenanthrenyl, and C$_{5-6}$ cycloalkyl;

X is a member selected from the group consisting of
—O—, —S—, —SO$_2$—, —CO—,

wherein R$^4$ is hydrogen, or C$_{1-6}$ alkyl and R$^7$ is hydrogen, C$_{1-6}$ alkyl, C$_{2-7}$ alkanoyl, or

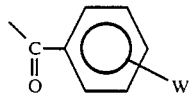

wherein W is hydrogen, halogen or alkoxy, and —CHR$^5$— wherein R$^5$ is hydrogen, CN, N$_3$ or NHR$^6$ with R$^6$ being R$^7$ or

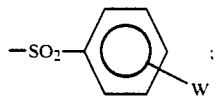

or Z and X taken together can be

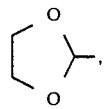

R$^1$ is hydrogen or C$_{1-4}$ alkyl;

R² is halogen;
R³ is hydrogen, C₁₋₄ alkoxy or C₁₋₄ alkylthio;
n is 1–3; and
m is 0 or 1; with the proviso that Z cannot be

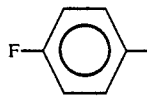

when X is $$-\overset{OH}{\underset{|}{CR^4}}-$$

or —CO—, while R³ is either hydrogen or C₁₋₄ alkoxy, or while m is 0.

2. A compound of claim 1 wherein Z is

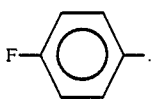

3. A compound of claim 1 wherein X is —CHR⁵—.

4. The compound of claim 1, 4-[5-fluoro-4-(methylthio)-2-pyrimidinyl]-1-[4-(4-fluorophenyl)-4-hydroxy-1-butyl]piperazine.

5. The compound of claim 1, 1-[5-cyano-5-(4-fluorophenyl)-1-pentyl]-4-(5-fluoro-2-pyrimidinyl) piperazine.

6. The compound of claim 1, 1-(4-fluorophenylbutyl)-4-(5-fluoro-2-pyrimidinyl)piperazine.

7. The compound of claim 1, 1-[3-(4-fluorophenyloxy)-propyl]-4-(5-fluoro-2-pyrimidinyl)-piperazine.

8. The compound of claim 1, 1-[3-(4-fluorophenylthio)-propyl]-4-(5-fluoro-2-pyrimidinyl)-piperazine.

9. The compound of claim 1, 1-[3-(1,3-dioxolan-2-yl) propyl]-4-(5-fluoro-2-pyrimidinyl)piperazine.

10. The compound of claim 1, 1-[3-(4-fluorophenylsulfonyl) propyl]4-(5-fluoro-2-pyrimidinyl)piperazine.

11. The compound of claim 1, 1-[4-acetamido-4-(4-fluorophenyl)butyl]-4-(5-fluoro-2-pyrimidinyl) piperazine.

12. The compound of claim 1, 1-[4-(4-fluorobenzamido)-4-(4-fluorophenyl)butyl]-4-(5-fluoro-2-pyrimidinyl) piperazine.

13. The compound of claim 1, 1-cyclohexyl-4-[4-(5-fluoro-2-pyrimidinyl)-1-piperazinyl]butanol.

14. The compound of claim 1, 1-[-4-(4-fluorophenyl)-4-(4-fluorophenylsulfonamido)butyl]-4-(5-fluoro-2-pyrimidin-yl)-piperazine.

15. The compound of claim 1, 1-(4-fluoronaphthyl)-4-[4-(5-fluoro-2-pyrimidinyl)-1-piperazinyl]butanol.

16. The compound of claim 1, 1-(4-fluoronaphthyl)-4-[4-(5-fluoro-2-pyrimidinyl)-1-piperazinyl]butanone.

17. The compound of claim 1, 4-[5-(5-fluoro-2-pyrimidinyl)-(1R,4R)-2,5-diazabicyclo[2.2.1]heptan-2-yl]-1-(4fluorophenyl)butanol.

18. The compound of claim 1, 4-[5-(5-fluoro-2-pyrimidinyl-(1S,4S)-2,5-diazabicyclo[2.2.1]heptan-2-yl]-1-(4-fluorophenyl)butanol.

19. The compound of claim 1, 1-(2-thienyl)-4-[4-(5-fluoro-2-pyrimidinyl)-1-piperazinyl]butanone.

20. The compound of claim 1, N-(1-(4-fluorophenyl)-4-(4-(5-fluoro-2-pyrimidinyl)-1-piperazinyl)-1-butyl) benzamide.

21. The compound of claim 1, 1-cyclohexyl-1-(4-fluorophenyl)-4-(4-(5-fluoro-2-pyrimidinyl)-1-piperazinyl)-1-butanol.

22. The compound of claim 1, 1-(4-cyclohexyl-1-butyl)-4-(5-fluoro-2-pyrimidinyl)piperazine.

23. The compound of claim 1, N-(1-(4-fluorophenyl)-4-(4-(5-fluoro-2-pyrimidinyl)-1-piperazinyl)-1-butyl 4-fluoro-1-naphthamide.

24. The compound of claim 1, N-(1-(4-fluoro-1-naphthyl)-4-(4-(5-fluoro-2-pyrimidinyl)-1-piperazinyl)-1-butyl) 4-fluorophenylsulfonamide.

25. The compound of claim 1, 1-(4-fluorophenyl)-4-(4-(5-fluoro-2-pyrimidinyl)-1-piperazinyl)-1-butyl acetate.

26. The compound of claim 1, 1-(4-fluorophenyl)-4-(4-(5-fluoro-2-pyrimidinyl)-1-piperazinyl)-1-butyl benzoate.

27. The compound of claim 1, 1-(2-(4-fluorophenyl)-1-ethyl)-4-(5-fluoro-2-pyrimidinyl)piperazine.

28. The compound of claim 1, 1-(4-fluorophenyl)-4-(4-(5-fluoro-2-pyrimidinyl)-1-piperazinyl)-1-butyl 4-fluorobenzoate.

29. The compound of claim 1, 1-(4-(4-fluoro-1-naphthyl)-1-butyl)-4-(5-fluoro-2-pyrimidinyl)piperazine.

30. The compound of claim 1, 1-(4-azido-4-(4-fluoro-1-naphthyl)-1-butyl)-4-(5-fluoro-2-pyrimidinyl)piperazine.

31. The compound of claim 1, 1-cyclohexyl-4-(4-(5-fluoro-2-pyrimidinyl)-1-piperazinyl)-1-butanone.

32. The compound of claim 1, N-(1-(4-fluoro-1-naphthyl)-4-(4-(5-fluoro-2-pyrimidinyl)-1-piperazinyl-1-butyl) 4-fluorobenzamide.

33. The compound of claim 1, N-(1-cyclohexyl-4-(4-(5-fluoro-2-pyrimidinyl-1-piperanzinyl)-1-butyl) 4-fluorophenyl-sulfonamide.

34. The compound of claim 1, N-(1-cyclohexyl-4-(4-(5-fluoro-2-pyrimidinyl-1-piperanzinyl-1-butyl) 4-fluorobenzamide.

35. The compound of claim 1, 1-(4-fluoro-1-naphthyl)-4-(4-(5-fluoro-2-pyrimidinyl)-1-piperazinyl)-1-butylamine.

36. The compound of claim 1, N-(1-(4-fluorophenyl)-4-(4-(5-fluoro-2-pyrimidinyl)-1-piperazinyl)-1-butyl) cyclohexane-carboxamide.

37. The compound of claim 1, 1-cyclohexyl-4-(4-(5-fluoro-2-pyrimidinyl)-1-piperazinyl)-1-butylamine.

38. The compound of claim 1, 1-[4-(4-fluorophenyl)-4-methoxybutyl]-4-(5-fluoropyrimidin-2-yl) piperazine.

39. The method for protecting brain cells from ischemia comprising systemic administration to a mammal suffering from ischemia or being susceptible to ischemia, of an effective ischemia-protective dose of a compound of claim 1.

40. A pharmaceutical composition suitable for systemic administration to a mammalian host comprising a pharmaceutical carrier and a compound of claim 1.

* * * * *